(12) United States Patent
Orlowski et al.

(10) Patent No.: US 7,589,066 B2
(45) Date of Patent: Sep. 15, 2009

(54) POTENT AND SPECIFIC IMMUNOPROTEASOME INHIBITORS

(75) Inventors: Robert Z. Orlowski, Chapel Hill, NC (US); Marian Orlowski, New York, NY (US)

(73) Assignees: The University of North Carolina at Chapel Hill, Chapel Hill, NC (US); Mount Sinai School of Medicine of New York University, New York, NY (US)

( * ) Notice: Subject to any disclaimer, the term of this patent is extended or adjusted under 35 U.S.C. 154(b) by 0 days.

(21) Appl. No.: 11/374,652

(22) Filed: Mar. 13, 2006

(65) Prior Publication Data

US 2006/0241056 A1 Oct. 26, 2006

Related U.S. Application Data

(60) Provisional application No. 60/660,596, filed on Mar. 11, 2005.

(51) Int. Cl.
    C07K 5/06 (2006.01)
(52) U.S. Cl. ...................................... 514/19
(58) Field of Classification Search .............. 514/2, 514/19; 530/330, 331
    See application file for complete search history.

(56) References Cited

U.S. PATENT DOCUMENTS

| 5,081,284 A | | 1/1992 | Higuchi et al. | |
|---|---|---|---|---|
| 5,780,454 A | | 7/1998 | Adams et al. | |
| 6,034,066 A | * | 3/2000 | Johnson et al. | ............... 514/18 |

OTHER PUBLICATIONS

International Search Report and the Written Opinion of the International Searching Authority, or the Declaration corresponding to the PCT Application No. PCT/US06/08835 dated Mar. 29, 2007.
Orlowski et al. "Evidence for the Presence of Five Distinct Proteolytic Components in the Pituitary . . ." *Biochemistry*, 32(6): 1563-1572, 1993.
Richardson et al. "A Phase 2 Study of Bortezomib in Relapsed, Refractory Myeloma", *N. Eng. J. Med.*, 348(26): 2609-17, Jun. 26, 2003.
Adams et al. "Proteasome Inhibitors: A Novel Class of Potent and Effective Antitumor Agents", *Cancer Research*, 59: 2615-22, Jun. 1, 1999.
Orlowski et al. "Phase Itrial of the Proteasome Inhibitor PS-341 in Patients With Refractory Hematologic Malignancies", *J.Clin.Onc.*, 20(22): 4420-4427, Nov. 15, 2002.
Voorhees et al. "The Proteasome as a Target for Cancer Therapy", *Clinical Cancer Research*, 9: 6316-6325, Dec. 15, 2003.
Vinitsky et al., "Inhibition of the Chymotrypsin-like Activity of the Pituitary Multicatalytic Proteinase Complex", *Biochemistry*, 31(39): 9421-9428, 1992.
El-Shami et al., "Induction Of Antitumor Immunity By Proteasome-Inhibited Syngeneic Fibroblasts Pulsed With A Modified TAA Peptide", *Int. J. Cancer*, 85: 236-242, 2000.
Wong et al., "Induction of Primary, Human Antigen-Specific Cytotoxic T Lymphocytes In Vitro Using Dendritic Cells Pulsed with Peptides", *Journal of Immunotherapy*, 21(1): 32-40, 1998.
Notification Concerning Transmittal of International Preliminary Report on Patentability for International Application No. PCT/US2006/008835 (Sep. 20, 2007).
Voorhees et al., "The Proteasome as a Target for Cancer Therapy", Clinical Cancer Research, vol. 9, pp. 6316-6325 (Dec. 15, 2003).
Richardson, et al., "A Phase 2 Study of Bortezomib in Relapsed, Refractory Myeloma", The New England Journal of Medicine, vol. 348, pp. 2609-2617 (Jun. 26, 2003).
Orlowski et al., "Phase I Trial of the Proteasome Inhibitor PS-341 in Patients with Refractory Hematologic Malignancies", Journal of Clinical Oncology, vol. 20, No. 22, pp. 4420-4427, (Nov. 15, 2002).
El-Shami et al., "Induction of Antitumor Immunity by Proteasome-Inhibited Syngeneic Fibroblasts Pulsed with a Modified TAA Peptide", Int. J. Cancer, vol. 85, pp. 236-242 (2000).
Adams et al., "Proteasome Inhibitors: A Novel Class of Potent and Effective Antitumor Agents", Cancer Research, vol. 59, pp. 2615-2622 (Jun. 1, 1999).
Wong et al., "Induction of Primary, Human Antigen-Specific Cytotoxic T Lymphocytes In Vitro Using Dendritic Cells Pulsed with Peptides", Journal of Immunotherapy, vol. 21, pp. 32-40 (1998).
Orlowski et al., "Evidence for the Presence of Five Distinct Proteolytic Components in the Pituitary Multicatalytic Proteinase Complex. Properties of Two Components Cleaving Bonds on the Carboxyl Side of Branched Chain and Small Neutral Amino Acids", Biochemistry, vol. 32, pp. 1563-1572 (1993).
Vinitsky et al., "Inhibition of the Chymotrypsin-like Activity of the Pituitary Multicatalytic Proteinase Complex", Biochemistry, vol. 31, pp. 9421-9428 (1992).

* cited by examiner

*Primary Examiner*—David Lukton
(74) *Attorney, Agent, or Firm*—Jenkins, Wilson, Taylor & Hunt, P.A.

(57) ABSTRACT

Compounds and methods of selectively inhibiting an immunoproteasome are described. Also described are methods of treating a cancer, an inflammation, and/or an autoimmune disease and methods of suppressing endogenous antigenic peptide generation by administering to a subject in need of treatment thereof a therapeutic amount of an immunoproteasome specific inhibitor.

1 Claim, 3 Drawing Sheets

POTENT AND SPECIFIC IMMUNOPROTEASOME INHIBITORS

CROSS REFERENCE TO RELATED APPLICATIONS

This application is based on and claims priority to U.S. Provisional Patent Application Ser. No. 60/660,596, filed Mar. 11, 2005, which is incorporated herein by reference in its entirety.

TECHNICAL FIELD

The currently disclosed subject matter relates to methods and compounds for selectively inhibiting immunoproteasome. The presently disclosed subject matter further relates to methods of treating a cancer, an inflammation, and/or an autoimmune disease, and methods of suppressing endogenous antigenic peptide generation by administering to a subject in need of treatment thereof a therapeutic amount of a proteasome inhibitor having specificity for the immunoproteasome.

ABBREVIATIONS

° C.=degrees Celsius
μM=micromolar
A=alanine
Ac=acetyl
BA=boronic acid
Boc=tert-butyloxycarbonyl
BrAAP=branched chain amino acid preferring
Cbz=benzyloxycarbonyl
CHO=aldehyde
ChT-L=chymotrypsin-like
DNA=deoxyribonucleic acid
EK=epoxyketone
F=phenylalanine
FDA=Food and Drug Administration
Fmoc=9-fluorenylmethyloxycarbonyl
G=glycine
hF=homophenylalanine
IPSI=immunoproteasome specific inhibitor
$K_i$=inhibition constant
L=leucine
LMP=low molecular weight proteins
MHC-1=major histocompatibility class 1
mVS=methyl vinyl sulfone
nL=norleucine
P=proline
pAB=para-amino-benzoate

BACKGROUND

The proteasome is an important cellular protease that is found in two forms: the constitutive proteasome, which contains active, e.g., catalytic, subunits termed X, Y, and Z, and the immunoproteasome, which contains different active subunits termed low molecular weight proteins (LMP), LMP-2, -7, and -10. The proteasome has emerged as an important chemotherapeutic target for a number of cancers, including hematologic malignancies in general, and multiple myeloma and non-Hodgkin's lymphoma in particular. See Voorhees, P. M., et al., *Clin. Cancer Res.*, 9: 6316-6325 (2003). Currently, the only proteasome inhibitor undergoing clinical testing is bortezomib, a non-specific proteasome inhibitor (VEL- CADE®, Millennium Pharmaceuticals, Inc., Cambridge, Mass., United States of America). See Adams. J., et al., *Cancer Res.*, 59: 2615-2622 (1999). Bortezomib, a dipeptide boronic acid (see Scheme 1, below), also known as PS-341, has shown promise as an anti-neoplastic agent and is now approved by the Food and Drug Administration (FDA) for patients with relapsed/refractory multiple myeloma who have had at least two prior therapies and progressed on the last of these.

Scheme 1. Structure of bortezomib.

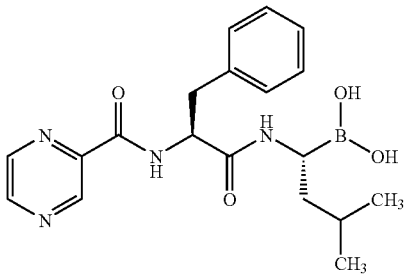

Bortezomib, however, is able to inhibit the function of both forms of the proteasome. Further, the use of bortezomib in patients typically is associated with substantial toxic effects, notably peripheral neuropathy, gastrointestinal side effects, and thrombocytopenia, which limit its clinical utility. See Orlowski, R. Z., et al., *J. Clin. Oncol.*, 20: 4420-4427 (2002); Richardson, P. G., et al., *N. Engl. J. Med.*, 348: 2609-2617 (2003). Thus, although bortezomib represents an important addition to the chemotherapeutic armamentarium, only 28% of patients with myeloma had partial responses or better in the phase II study that led to its FDA approval. Novel proteasome inhibitors with improved anti-tumor activity and an improved toxicity profile are needed.

While the proteasome is present in both the cytoplasm and nucleus of all cells, studies have revealed that it is not a static structure. Exposure of cells to cytokines, such as gamma-interferon, causes at least partial replacement of the three catalytic subunits X, Y, and Z, with LMP-2, -7, and -10. See Fruh, K., et al., *EMBO J.*, 13: 3236-3244 (1994); Akiyama, K., et al., *Science*, 265: 1231-1234 (1994); Akiyama, K., et al., *FEBS Lett.*, 343: 85-88 (1994); Belich. M. P., et al., *Curr. Biol.*, 4: 769-776 (1994); and Tanaka, K., *J. Leukoc. Biol.*, 56: 571-575 (1994). The LMP-containing proteasome has been referred to in the past as the immunoproteasome, because of initial thoughts that it might play a role generating antigens that were presented in the context of major histocompatibility class I (MHC-1) molecules as part of the immune response. See Teoh, C. Y. and Davies, K. J., *Arch. Biochem. Biophys.*, 423: 88-96 (2004).

These proteasomes also are constitutively expressed in cell lines derived from hematopoietic precursors, and could possibly be targeted specifically by inhibitors that recognize only the LMP-type proteasome. Furthermore, such agents would spare proteasomes in gastrointestinal or neural tissues, possibly decreasing drug-related toxicities, such as those seen with non-specific agents. Additional potential applications of these agents would include their use as immune suppressive drugs to treat auto-immune and other inflammatory conditions, including graft rejection and graft-versus-host disease, or as part of vaccine therapy to specifically suppress the generation of endogenous antigenic peptides. See Wong, C., et al., *J. Immunother.*, 21: 3240 (1998); and El-Shami, K. M., et al., *Int J. Cancer*, 85: 236-242 (2000). To date, however, the identification of such specific inhibitors has not yet been reported in the art.

SUMMARY

The presently disclosed subject matter provides compounds that have specificity for the immunoproteasome. In some embodiments, the compounds have comparatively little to no ability to inhibit the constitutive proteasome. In some embodiments, the presently disclosed subject matter provides a compound having a 10-fold or greater preference for inhibiting an immunoproteasome as compared to a constitutive proteasome, said compound having a structure of Formula (I):

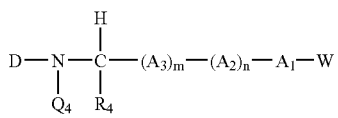

wherein:
n is an integer from 0 to 1;
m is an integer from 0 to 1;
D is selected from the group consisting of H, alkyl, branched alkyl, aralkyl, aryl, acyl, aroyl, alkoxycarbonyl, aralkyloxycarbonyl and aryloxycarbonyl;
$A_1$ is selected from the group consisting of:

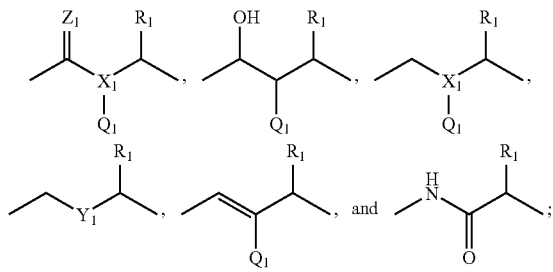

$A_2$ is selected from the group consisting of:

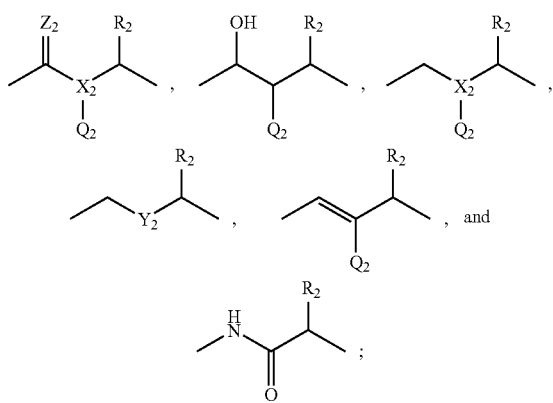

$A_3$ is selected from the group consisting of:

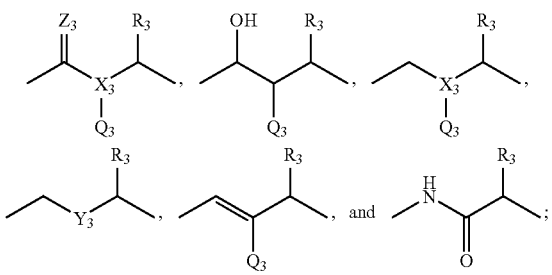

$Z_1$, $Z_2$, and $Z_3$ are independently selected from O and S;
$Y_1$, $Y_2$, and $Y_3$ are independently selected from O or S;
$X_1$, $X_2$, $X_3$, and $X_4$ are independently selected from N and CH;
$Q_1$, $Q_2$, $Q_3$, and $Q_4$ are independently selected from the group consisting of H and alkyl; and
$R_1$, $R_2$, $R_3$, and $R_4$ are independently selected from H, alkyl, branched alkyl, aryl, aralkyl, and substituted alkyl; or
one or more of $Q_2$ and $R_2$ together, $Q_3$ and $R_3$ together, and $Q_4$ and $R_4$ together are $C_2$-$C_5$ alkylene; and
W is selected from the group consisting of:

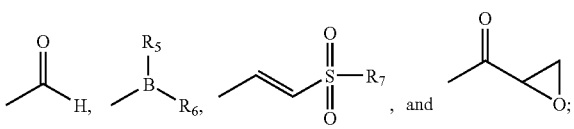

wherein:
$R_5$ and $R_6$ are independently selected from hydroxy, alkoxy, aralkoxy, and aryloxy, or $R_5$ and $R_6$ together form a di-oxyalkylene group having two oxy radicals separated by at least two connecting atoms in a chain or ring, said chain or ring comprising carbon atoms and optionally a heteroatom or heteroatoms, N, S, or O; and
$R_7$ is selected from alkyl, aryl, and substituted aryl;
or a pharmaceutically acceptable salt thereof.
In some embodiments, each of $A_1$, $A_2$, and $A_3$ comprise an amide bond and the compound of Formula (I) is a compound of Formula (II):

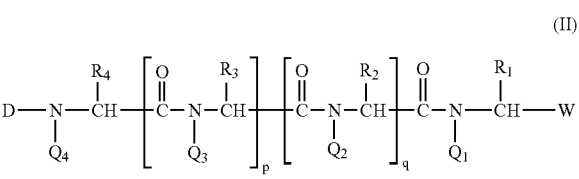

wherein:
p is an integer from 0 to 1;
q is an integer from 0 to 1;
D is selected from the group consisting of H, alkyl, branched alkyl, aralkyl, aryl, acyl, aroyl, alkoxycarbonyl, aralkyloxycarbonyl and aryloxycarbonyl;
each $Q_1$, $Q_2$, $Q_3$, and $Q_4$ is selected from H and alkyl;
each $R_1$, $R_2$, $R_3$, and $R_4$ is selected from H, alkyl, branched alkyl, aryl, aralkyl, and substituted alkyl; or one or more of $R_2$ and $Q_2$ together, $R_3$ and $Q_3$ together and $R_4$ and $Q_4$ together are $C_2$-$C_5$ alkylene; and W is selected from the group consisting of:

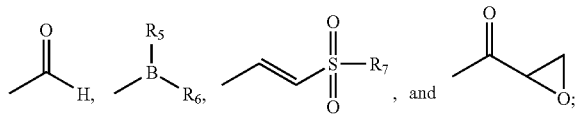

wherein:
$R_5$ and $R_6$ are independently selected from hydroxy, alkoxy, aralkoxy, and aryloxy, or $R_5$ and $R_6$ together form a di-oxyalkylene group having two oxy radicals separated by at least two connecting atoms in a chain or ring, said chain or ring comprising carbon atoms and optionally a heteroatom or heteroatoms, N, S, or O; and $R_7$ is selected from alkyl, aryl, and substituted aryl;

or a pharmaceutically acceptable salt thereof.

In some embodiments, D is selected from the group consisting of aralkyloxycarbonyl, alkoxycarbonyl, and acyl. In some embodiments, D is selected from the carbobenzyloxy (Cbz) group, the 9-fluorenylmethyloxycarbonyl (Fmoc) group, the tert-butyloxycarbonyl (Boc) group, and the acetyl (Ac) group. In some embodiments, D is the carbobenzyloxy (Cbz) group.

In some embodiments, W is aldehyde (CHO).

In some embodiments, $R_1$ is selected from the group consisting of alkyl, branched alkyl, and aralkyl. In some embodiments, $R_1$ is benzyl. In some embodiments, $R_1$ is n-butyl.

In some embodiments, p and q are each 0, and $R_4$ is selected from benzyl, isobutyl, methyl, and phenylethyl.

In some embodiments, p and q are each 1, $R_2$ is selected from methyl and benzyl, $R_3$ and $Q_3$ together are propylene, and $R_4$ is H.

In some embodiments, q is 1, p is 0, $R_2$ is selected from isobutyl and benzyl, and $R_4$ is selected from isobutyl and H.

In some embodiments, the compound of Formula (I-II) is selected from the group consisting of:
N-carbobenzyloxy-leucyl-norleucinal,
N-carbobenzyloxy-phenylalanyl-phenylalanylal,
N-carbobenzyloxy-homophenylalanyl-phenylalanylal,
N-carbobenzyloxy-leucyl-phenylalanylal,
N-carbobenzyloxy-alanyl-phenylalanylal,
N-carbobenzyloxy-glycyl-prolyl-alanyl-phenylalanylal,
N-carbobenzyloxy-glycyl-prolyl-phenylalanyl-phenylalanylal,
N-carbobenzyloxy-leucyl-leucyl-phenylalanylal,
N-carbobenzyloxy-glycyl-phenylalanyl-phenylalanylal,
N-carbobenzyloxy-leucyl-norleucine boronic acid,
N-carbobenzyloxy-phenylalanyl-phenylalanine boronic acid,
N-carbobenzyloxy-homophenylalanyl-phenylalanine boronic acid,
N-carbobenzyloxy-leucyl-phenylalanine boronic acid,
N-carbobenzyloxy-alanyl-phenylalanine boronic acid,
N-carbobenzyloxy-glycyl-prolyl-alanyl-phenylalanine boronic acid,
N-carbobenzyloxy-glycyl-prolyl-phenylalanyl-phenylalanine boronic acid,
N-carbobenzyloxy-leucyl-leucyl-phenylalanine boronic acid,
N-carbobenzyloxy-glycyl-phenylalanyl-phenylalanine boronic acid,
N-carbobenzyloxy-leucyl-norleucine methyl vinyl sulfone,
N-carbobenzyloxy-phenylalanyl-phenylalanine methyl vinyl sulfone,
N-carbobenzyloxy-homophenylalanyl-phenylalanine methyl vinyl sulfone,
N-carbobenzyloxy-leucyl-phenylalanine methyl vinyl sulfone,
N-carbobenzyloxy-alanyl-phenylalanine methyl vinyl sulfone,
N-carbobenzyloxy-glycyl-prolyl-alanyl-phenylalanine methyl vinyl sulfone,
N-carbobenzyloxy-glycyl-prolyl-phenylalanyl-phenylalanine methyl vinyl sulfone,
N-carbobenzyloxy-leucyl-leucyl-phenylalanine methyl vinyl sulfone,
N-carbobenzyloxy-glycyl-phenylalanyl-phenylalanine methyl vinyl sulfone,
N-carbobenzyloxy-leucyl-norleucine epoxy ketone,
N-carbobenzyloxy-phenylalanyl-phenylalanine epoxy ketone,
N-carbobenzyloxy-homophenylalanyl-phenylalanine epoxy ketone,
N-carbobenzyloxy-leucyl-phenylalanine epoxy ketone,
N-carbobenzyloxy-alanyl-phenylalanine epoxy ketone,
N-carbobenzyloxy-glycyl-prolyl-alanyl-phenylalanine epoxy ketone,
N-carbobenzyloxy-glycyl-prolyl-phenylalanyl-phenylalanine epoxy ketone,
N-carbobenzyloxy-leucyl-leucyl-phenylalanine epoxy ketone, and
N-carbobenzyloxy-glycyl-phenylalanyl-phenylalanine epoxy ketone.

In some embodiments, the presently disclosed subject matter provides a method for selectively inhibiting immunoproteasome in a cell by contacting the cell with a compound of Formula (I-II). In some embodiments, the cell is in a subject. In some embodiments, the subject is a human.

In some embodiments, the compound of Formula (I-II) has a greater than 100-fold preference for inhibiting the immunoproteasome as compared to the constitutive proteasome. In some embodiments, the compound of Formula (I-II) has $K_i$ of 25 μM or less for an immunoproteasome.

In some embodiments, the presently disclosed subject matter provides a method of treating cancer in a subject in need of treatment thereof by administering to the subject a therapeutic amount of a proteasome inhibitor having specificity for the immunoproteasome. In some embodiments, the proteasome inhibitor is a compound of Formula (I-II). In some embodiments, the cancer is selected from the group consisting of multiple myeloma, Hodgkin's lymphoma, non-Hodgkin's lymphoma, acute leukemia, and chronic leukemia. In some embodiments, the method comprises administering a therapeutic amount of a proteasome inhibitor and one or more additional anti-cancer treatment agents.

In some embodiments, the presently disclosed subject matter provides a method of treating inflammation in a subject in need of treatment thereof, the method comprising administering to the subject a therapeutic amount of a proteasome inhibitor having specificity for the immunoproteasome. In some embodiments, the inflammation is related to one of the group consisting of transplantation rejection, arthritis, rheumatoid arthritis, infection, dermatosis, inflammatory bowel disease, asthma, osteoporosis, osteoarthritis, psoriasis, and restenosis.

In some embodiments, the presently disclosed subject matter provides a method of treating an auto-immune disease in a subject in need of treatment thereof, the method comprising administering to the subject a therapeutic amount of a proteasome inhibitor having specificity for the immunoproteasome. In some embodiments the autoimmune disease is selected from the group consisting of rheumatoid arthritis, multiple sclerosis, systemic lupus erythromatosis (SLE), scleroderma, diabetes, inflammatory bowel disease, psoriasis, atherosclerosis, graft versus host disease, and tissue transplant rejection.

In some embodiments, the presently disclosed subject matter provides a method of suppressing endogenous antigenic peptide generation in a subject in need thereof, the method comprising administering to the subject a therapeutic amount of a proteasome inhibitor having specificity for an immunoproteasome.

In some embodiments, the presently disclosed subject matter provides a pharmaceutical formulation comprising a compound having a 10-fold or greater preference for inhibiting an immunoproteasome as compared to a constitutive proteasome and a pharmaceutically acceptable carrier.

Accordingly, it is an object of the presently disclosed subject matter to provide methods and compositions for selectively inhibiting an immunoproteasome in a cell.

It is another object of the presently disclosed subject matter to provide a method of treating one or more of a cancer, inflammation, or an auto-immune disease in a subject in need thereof. It is a further object of the presently disclosed subject matter to provide a method of endogenous antigenic peptide generation in a subject in need thereof.

Certain aspects and objects of the presently disclosed subject matter having been stated hereinabove, which are addressed in whole or in part by the presently disclosed subject matter, other aspects and objects will become evident as the description proceeds when taken in connection with the accompanying Drawings and Examples as best described herein below.

DETAILED DESCRIPTION

Figure 1:
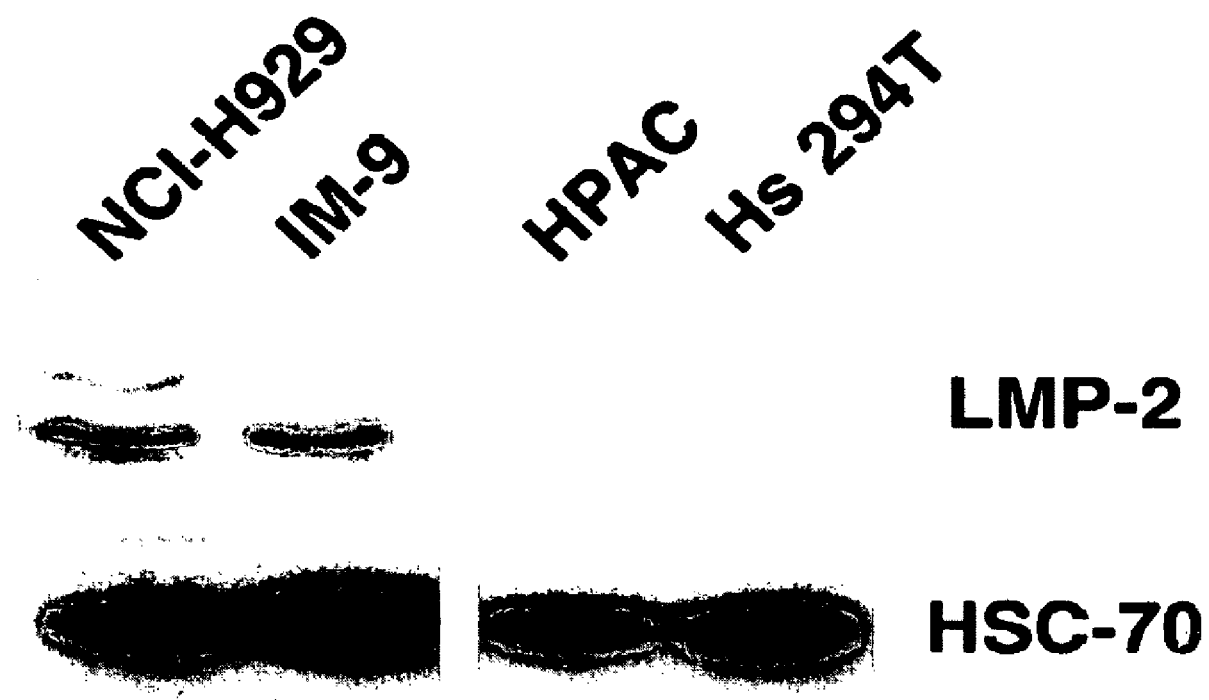
FIG. 1 is a Western blot showing the expression of the LMP-2 proteasome subunit in NCI-H929 human myeloma cells, IM-9 human B-lymphoblasts, HPAC human pancreatic adenocarcinoma cells, and Hs 294T human melanoma cells.

The presently disclosed subject matter will now be described more fully hereinafter with reference to the accompanying Drawings and Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

The term "standard amino acid" refers to any of the twenty standard L-amino acids commonly found in naturally occurring peptides. "Nonstandard amino acid" means any amino acid, other than the standard amino acids, regardless of whether it is prepared synthetically or derived from a natural source.

The term "peptide bond" refers to a bond formed through a condensation reaction between an amine and a carboxyl group, with the loss of water, to form an amide. The amide linkage between two amino acids is thus referred to as "a peptide bond." An example of a peptide bond formed between two amino acids is as follows:

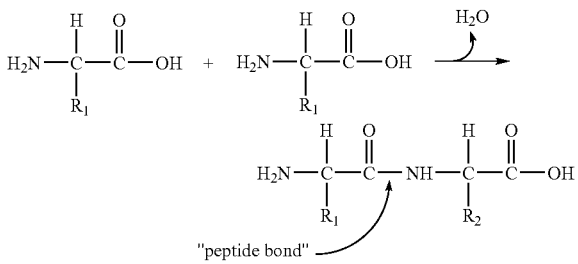

Accordingly, any number of amino acids can be bonded in a like manner in a continuous chain.

The term "peptide" refers to any polymer of amino acids linked by amide bonds between the amino group of each amino acid and the carboxyl group of the neighboring amino acid. Each amino acid unit making up the peptide is referred to as a "residue." Thus the term "amino acid residue" refers to the radical or diradical of one of the 20 standard amino acids or of a nonstandard amino acid that results from the loss of a proton from the amine group, the loss of the hydroxyl from the carboxylic acid group, or the loss of both a proton from the amine group and the hydroxyl from the carboxylic acid group.

The terms "pseudopeptide bond" and "peptide isostere" can be used interchangeably to refer to a bond used to replace the peptide bond of a polypeptide. For example, the —C(=O)—NH— bond can be reduced to form a —CH$_2$—NH— group or the —C(=O)—NH— bond can be replaced with a hydroxyethylene group, —C(OH)=CH$_2$—. In general, but not always, such pseudopeptide bonds will be more resistant to chemical or enzymatic hydrolysis than the corresponding peptide bond. Thus, a "pseudopeptide" refers to a peptide containing one or more pseudopeptide bond.

The term "dipeptide" refers to an amide comprising two amino acid residues.

The term "tripeptide" refers to a compound comprising three amino acid residues and two peptide bonds.

The term "tetrapeptide" refers to a compound comprising four amino acid residues and three peptide bonds.

The term "oligopeptide" refers to peptides comprising a short chain of amino acid residues, such as but not limited to, about three to about twenty amino acid residues, including but not limited to, about four to about ten amino acid residues.

Generally, a "polypeptide" is a peptide comprising many amino acid residues, and typically has a molecular weight less than about 5000. Further, a "protein" comprises a larger number of amino acid residues, with molecular weights ranging from about 6000 to about 40,000,000. As used herein, the term "polypeptide" means any polymer comprising any of the natural or unnatural protein amino acids, regardless of its size. Although "protein" is often used in reference to relatively large polypeptides, and "peptide" is often used in reference to small polypeptides, usage of these terms in the art overlaps and varies. Accordingly, the term "polypeptide" as used herein refers to peptides, polypeptides and proteins, unless otherwise noted. Thus, as used herein, the terms "protein", "polypeptide" and "peptide" are used interchangeably.

The end of the peptide with the free amino group is called the "N terminus" and the end of the peptide with the free carboxyl group is called the "C terminus."

Following the convention known in the art, a peptide is named beginning at the N terminus, and the names of the amino acid residue(s) involved in the amide linkages (all except the last residue) are given the -yl suffix. For example, following this convention, the following dipeptide would be named: leucylphenylalanine:

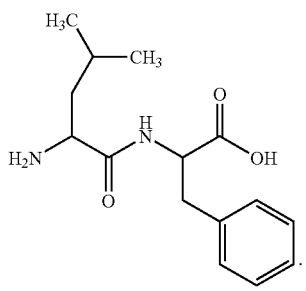

Further, modification of the C terminus of the phenylalanine residue of the dipeptide leucylphenylalanine referenced immediately above by reduction of the carboxyl group to an aldehyde (CHO, which can be represented as —CH(=O)) produces leucylphenylalanal:

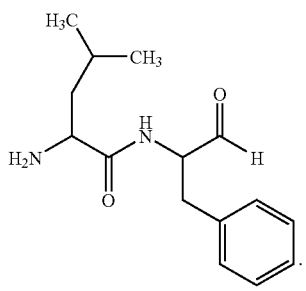

In some embodiments of the presently disclosed subject matter, the C terminus of a particular amino acid residue can be modified by a boronic acid group (—B(OH)$_2$) or an ester of a boronic acid group. In some embodiments of the presently disclosed subject matter, the C terminus of a particular amino acid residue can be modified by a vinyl sulfone (VS) group:

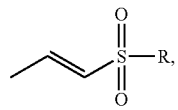

wherein the R group is an alkyl, aralkyl, aryl or substituted aryl group, for example a methyl or para-hydroxyphenyl group. In some embodiments of the presently disclosed subject matter, the C terminus of a particular amino acid residue can be modified by an epoxy ketone (EK) group:

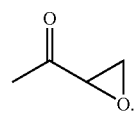

As used herein the term "peptide analog" can refer to peptides with modified N- or C-termini (i.e., a peptide or pseudopeptide with an N-terminus other than NH$_2$ and/or a C-terminus other than carboxylic acid). Thus, for example, a peptide analog can refer to a Cbz-, Boc, Ac, or Fmoc protected peptide, to a peptide vinyl sulfone, a peptide aldehyde, a peptide boronic acid or ester, to a peptide epoxy ketone, or to a combination thereof. "Peptide analog" can also be used to refer to pseudopeptides and to pseudopeptides with modified N- or C-termini.

As used herein the term "alkyl" refers to C$_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a C$_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to C$_{1-8}$ straight-chain alkyls. In other embodiments, "alkyl" refers, in particular, to C$_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxy, aryloxy, alkoxy, alkylthio, arylthio, aralkyloxy, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxy, hydroxy, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxy, alkoxy, aryloxy, aralkyloxy, carboxyl, acyl, halo, nitro, alkoxycarbonyl, aryloxycarbonyl, aralkoxycarbonyl, acyloxy, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxy, hydroxy, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkylene" refers to a bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—($CH_2$)$_3$—); cyclohexylene (—$C_6H_{10}$—); —CH=CH—CH=CH—; —CH=CH—$CH_2$—; ($CH_2$)$_q$—N(R)—($CH_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxy (—O—$CH_2$—O—); and ethylenedioxy (—O—($CH_2$)$_2$—O—). An alkylene group can have about 2 to about 5 carbon atoms and can further have 6-20 carbons.

The term "di-oxyalkylene" refers to the —O-alkylene-O— group, wherein alkylene is defined as herein above.

The term "amino" refers to the —$NH_2$ group.

The term "oxy" as used herein refers to an oxygen atom.

The term "oxo" refers to a double-bonded oxygen atom, (=O).

The term "carbonyl" refers to the —C(=O)— group.

The term "carboxyl" refers to the —COOH group.

The term "acyl" refers to the —C(=O)-alkyl group. An example of an acyl group is acetyl (—C(=O)—$CH_3$).

The term "aroyl" refers to the —C(=O)-aryl group.

The terms "halo" and "halide" as used herein refer to fluoro, chloro, bromo, and iodo groups.

The term "hydroxy" or "hydroxyl" refers to the —OH group.

"Alkoxy" refers to an alkyl-O— group wherein alkyl is as previously described. The term "alkoxy" as used herein can refer to $C_{1-20}$ inclusive, linear, branched, or cyclic, saturated or unsaturated oxy-hydrocarbon chains, including, for example, methoxy, ethoxy, propoxy, isopropoxy, butoxy, t-butoxy, and pentoxy.

"Aryloxy" refers to an aryl-O— group wherein the aryl group is as previously described, including a substituted aryl. For example, the term "aryloxy" as used herein can refer to phenyloxy or napthyloxy, and alkyl, substituted alkyl, halo, hydroxy, or alkoxy substituted phenyloxy or napthyloxy.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxy" refers to an aralkyl-O— group wherein the aralkyl group is as previously described. An exemplary aralkyloxy group is benzyloxy.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and napthyloxy-carbonyl.

"Aralkoxycarbonyl" refers to an aralkyl-O—CO— group. An exemplary aralkoxycarbonyl group is benzyloxycarbonyl.

The term "amino-group protecting moiety" as used herein, refers to any group used to derivatize an amino group, especially an N-terminal amino group of a peptide or amino acid. Such groups include, without limitation, alkyl, acyl, alkoxycarbonyl, aminocarbonyl, and sulfonylmoieties. The term "amino-group protecting moiety" is not intended to be limited to those particular protecting groups commonly employed in organic synthesis, nor is it intended to be limited to groups that are readily cleavable. However, in some cases the amino-group protecting moiety will be a group commonly employed in organic synthesis, particularly in peptide synthesis. Thus, examples of suitable groups include, but are not limited to, acyl protecting groups, for example, formyl, dansyl, acetyl (Ac), benzoyl (Bz), trifluoroacetyl, succinyl (Suc) and methoxysuccinyl (MeOSuc); aralkyoxycarbonyl groups, for example, benzyloxycarbonyl (Cbz) and fluorenylmethyloxycarbonyl (Fmoc); and alkoxycarbonyl groups, for example, tert-butoxycarbonyl (Boc) or adamantyloxycarbonyl.

The presence or absence of any R, A, X, Q, Z, or Y or any other named group or atom in a structure and the number of any R, A, X, Q, Z, Y or other named group or atom is determined by the value of the integer n, m, p or q placed outside of brackets or parentheses surrounding the R, A, X, Q, Z, Y or other indicated atom, group or combination of such elements. For example, in the formula:

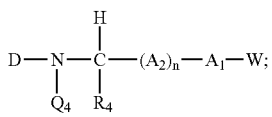

refers to a structure that when n is 0, $A_2$ is not present and $A_1$ is directly bonded to C to form compounds having the structure:

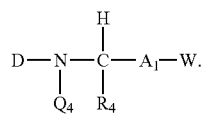

When n is 1, $A_2$ is present, and the compounds have the structure:

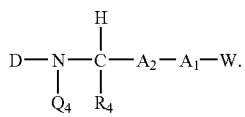

When the term "independently selected" is used, the substituents being referred to (e.g., R groups, such as groups $R_1$ and $R_2$, or groups X and Y), can be identical or different. For example, both $R_1$ and $R_2$ can be substituted alkyls, or $R_1$ can be hydrogen and $R_2$ can be a substituted alkyl, and the like.

A named "R", "X", "A", "B," "D", "W", "Z", "Y" or "Q" group will generally have the structure that is recognized in the art as corresponding to a group having that name, unless specified otherwise herein. For the purposes of illustration, certain representative "R", "X", "W", "Z", "Y", and "A" groups as set forth above are defined below. These definitions are intended to supplement and illustrate, not preclude, the definitions that would be apparent to one of ordinary skill in the art upon review of the present disclosure.

As used herein, the terms "hemopoietic" and "hematopoietic" are used interchangeably to mean all blood cells including myeloid and lymphoid cells. Myeloid cells include erythrocytes (i.e., red blood cells), macrophages, monocytes, granulocytes including neutrophils, eosinophils and basophils, mast cells, megakaryoctyes, platelets and dendritic cells, and lymphoid cells include T and B lymphocytes, thymic dendritic cells and natural killer (NK) cells.

As used herein, the term "$IC_{50}$" is the amount of compound required to inhibit 50% of the activity of a given enzyme, for example, an immunoproteasome or a constitutive proteasome.

II. Immunoproteasome-Specific Inhibitors

Upon exposure to various stimuli, including interferon (IFN)-γ, tumor necrosis factor (TNF)-γ, and lipopolysaccharide (LPS), alternative catalytic subunits are incorporated into the proteasome, which is then termed the immunoproteasome. Immunoproteasome-specific inhibitors are potentially valuable research tools to help dissect the role of the immunoproteasome relative to the constitutive proteasome in many cellular processes. Further, from a therapeutic perspective, immunoproteasome inhibitors have the promise of being active against immunoproteasome-expressing tumors with greater efficacy and a greater therapeutic index, since it is likely that much of the toxicity of non-specific proteasome inhibitors, such as bortezomib, is due to constitutive proteasome inhibition in non-target tissues. Given the known expression profile of immunoproteasome subunits, immunoproteasome-specific inhibitors would be particularly active against multiple myeloma, Hodgkin's and non-Hodgkin's lymphomas, and both acute and chronic leukemias. Also, because of the role of the immunoproteasome in the immune response, these inhibitors could be more efficient than previously disclosed non-specific proteasome inhibitors as anti-inflammatory agents, for auto-immune diseases, for graft rejection in a transplant setting, and in conjunction with vaccine strategies to suppress endogenous antigenic peptide generation.

Disclosed herein is a class of peptide analogs that have specificity for the immunoproteasome. In some embodiments, the peptide analogs selectively inhibit the immunoproteasome as compared to the constitutive proteasome. In some embodiments, the peptide analogs have a 10-fold or greater preference for inhibiting an immunoproteasome as compared to a constitutive proteasome and have a structure of Formula (I):

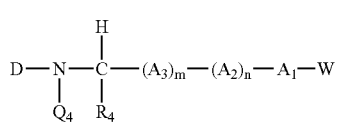

wherein:

n is an integer from 0 to 1;

m is an integer from 0 to 1;

D is selected from the group consisting of H, alkyl, branched alkyl, aralkyl, aryl, acyl, aroyl, alkoxycarbonyl, aralkyloxycarbonyl and aryloxycarbonyl;

$A_1$ is selected from the group consisting of:

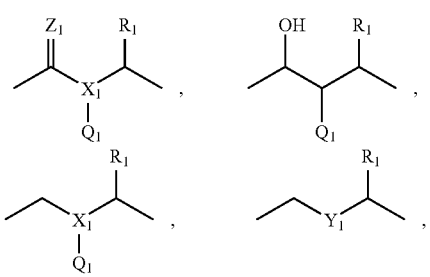

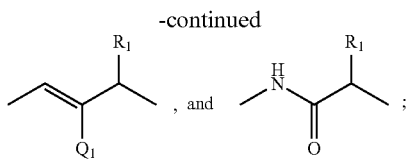

$A_2$ is selected from the group consisting of:

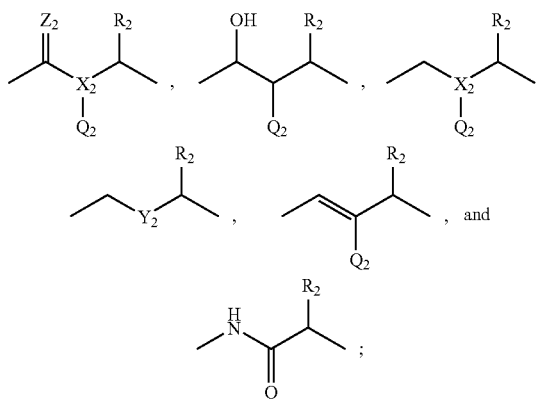

$A_3$ is selected from the group consisting of:

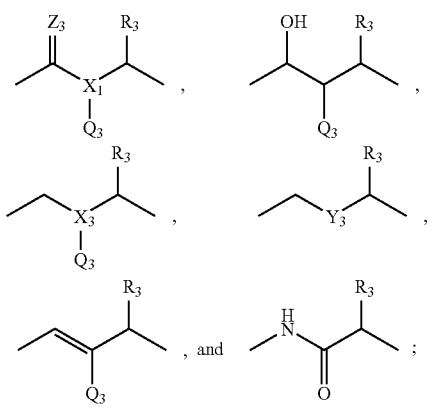

$Z_1$, $Z_2$, and $Z_3$ are independently selected from O and S;

$Y_1$, $Y_2$, and $Y_3$ are independently selected from O or S;

$X_1$, $X_2$, $X_3$, and $X_4$ are independently selected from N and CH;

$Q_1$, $Q_2$, $Q_3$, and $Q_4$ are independently selected from the group consisting of H and alkyl; and $R_1$, $R_2$, $R_3$, and $R_4$ are independently selected from H, alkyl, branched alkyl, aryl, aralkyl, and substituted alkyl; or one or more of $Q_2$ and $R_2$ together, $Q_3$ and $R_3$ together, and $Q_4$ and $R_4$ together are $C_2$-$C_5$ alkylene; and W is selected from the group consisting of:

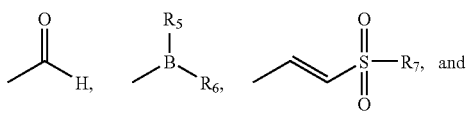

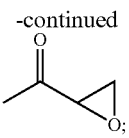

wherein:

$R_5$ and $R_6$ are independently selected from hydroxy, alkoxy, aralkoxy, and aryloxy, or $R_5$ and $R_6$ together form a di-oxyalkylene group having two oxy radicals separated by at least two connecting atoms in a chain or ring, said chain or ring comprising carbon atoms and optionally a heteroatom or heteroatoms, N, S, or O; and $R_7$ is selected from alkyl, aryl, and substituted aryl;

or a pharmaceutically acceptable salt thereof.

Thus the compounds of Formula (I) can be dipeptide, tripeptide, and tetrapeptide analogs, optionally N-terminal protected, wherein the C-terminal is an aldehyde, a boronic acid or ester, a vinyl sulfone, or an epoxy ketone. Compounds of Formula (I) also include pseudopeptides wherein one or more of the peptide bonds of the di-, tri-, or tetrapeptide has been replaced by a peptide isostere.

Peptide isosteres, also referred to herein as pseudopeptide bonds, can be used to improve the hydrolytic stability of the peptide analog to chemical or enzymatic hydrolysis, either in vitro or in vivo. The use of a peptide isostere also can be used to improve the solubility of a peptide analog. In some embodiments, the peptide isostere will resemble the peptide bond in one or more of geometry (i.e., three-dimensional shape or sterics), charge distribution (i.e., electronics), and hydrogen bonding ability. Suitable peptide isosteres include: ketomethylene (—C(=O)CH₂—), reduced amide (—CH₂NH—), carba (—CH₂CH₂—), thioamide (—C(=S)NH—), ether (—CH₂O—), thioether (—CH₂S—), E-alkene (—CH=CH—), retro-inverso (—NHC(=O)—), and hydroxyethylene (—CH(OH)CH₂—).

Peptide isosteres, their properties, and synthetic methods for preparing pseudopeptides containing them have recently been reviewed. See Venkatesan, N., and Kim, B. H., *Curr. Med. Chem.*, 9, 2243-2270 (2002). Reduced amides can be prepared using various reducing agents known in the art or by the reductive amination of amine aldehydes or amino acids, while thiamides can be prepared by treating the amide with Lawesson's reagent (i.e., 2,4-Bis-(4-methoxy-phenyl)-1,3-dithia-2,4-diphosphetane 2,4-disulfide). See Venkatesan, N., and Kim, B. H., *Curr. Med. Chem.*, 9, 2243-2270 (2002).

In some embodiments, the nitrogen atom of the peptide or peptide isostere can be substituted with an alkyl group. Thus, in some embodiments, an alkylated amide (—C(=O)NR—) can be used as a peptide isostere. In some embodiments, the peptide bond is replaced by a peptide isostere wherein a carbon atom replaces the nitrogen atom of the peptide bond (i.e., carba, ketomethylene, or hydroxyethylene group and the like), and that carbon atom can be further substituted with an alkyl group. In some embodiments, the nitrogen atom of the peptide bond or peptide isostere can be one of two atoms substituted with an alkylene group. For example, the peptide bond or peptide isostere can be part of a proline residue.

In some embodiments, each R group present (i.e., $R_1$, $R_2$, $R_3$, and $R_4$) is a side chain group of a nonpolar standard or nonstandard amino acid. In some embodiments, the nonpolar standard amino acid is glycine, alanine, valine, leucine, isoluecine, proline, methionine, phenylalanine or tryptophan. In some embodiments, the nonpolar nonstandard amino acid is one of: homophenylalanine, norleucine, 1-aminocyclopropane carboxylic acid, 1-aminocyclobutane carboxylic acid, 1-amino-2-phenylcyclopropane carboxylic acid, 2-amino-4-cyclohexylbutyric acid, 3-cyclohexylalanine (Cha), 3-(9-anthryl)alanine, 3-cyclopentylalanine, α-napthylmethylproline, α-benzylproline, α-methylproline, α-propylproline, α-(4-methylbenzyl)proline, 3,3-diphenylalanine, 3-(1-napthyl)alanine, 3-(2-napthyl)alanine, 3-styrylalanine, 2-(amino)isobutyric acid, 2-cyclohexylglycine, 2-amino-3,3-dimethylbutyric acid (Tle), 2-phenylglycine (Phg), 2-methylphenylalanine, 3-methylphenylalanine, and 4-methylphenylalanine. In some embodiments, the side chain of the nonpolar standard or nonstandard amino acid is composed of only carbon and hydrogen atoms.

In some embodiments, $R_1$, $R_2$, $R_3$, and $R_4$ are independently selected from the side chain groups of leucine (Leu or L), glycine (Gly or G), phenylalanine (Phe or F), alanine (Ala or A), norleucine (nL), or homoalanine (hF). Thus, in some embodiments, $R_1$, $R_2$, $R_3$, and $R_4$ are independently selected from isobutyl, H, benzyl, methyl, n-butyl, and phenylethyl. In some embodiments, $R_1$ is benzyl. In some embodiments, $R_1$ is n-butyl.

Alternatively, one or more R group can together with an adjacent nitrogen substituent (i.e., $Q_1$, $Q_2$, $Q_3$, or $Q_4$) be a $C_2$-$C_6$ alkylene group. In some embodiments, the alkylene group is propylene (i.e. $C_3$ alkylene) and the peptide or psuedopeptide residue containing the alkylene group is based on the amino acid proline (Pro or P). In some embodiments, $R_3$ and $Q_3$ together are $C_3$ alkylene.

In some embodiments, D is an amino-protecting group. In some embodiments, D is the Cbz, Ac, Fmoc or Boc. In some embodiments, D is Cbz.

In some embodiments, W is an aldehyde (CHO), having the structure:

In some embodiments, W is a boronic acid or the ester of a boronic acid. Thus, in some embodiments, $R_5$ and $R_6$ are selected from hydroxy, alkoxy, aralkoxy, and aryloxy. In some embodiments, $R_5$ and $R_6$ together form a di-oxyalkylene group having two oxy radicals separated by at least two connecting atoms in a chain or ring, said chain or ring comprising carbon atoms and optionally a heteroatom or heteroatoms, N, S, or O. For example, the di-oxyalkylene group can be the formed by the double deprotonation of pinacol, perfluoropinacol, pinanediol, ethylene glycol, diethylene glycol, catechol, 1,2-cyclohexanediol, 1,3-propanediol, 2,3-butanediol, glycercol, diethanolamine or another amino alcohol.

In some embodiments, W is a vinyl sulfone. In some embodiments, $R_7$ is methyl and W is a methyl vinyl sulfone (mVS). In some embodiments, $R_7$ is para-hydroxyphenyl ($-C_6H_5OH$) and W is a phenolic vinyl sulfone (pVS).

In some embodiments, m and n are each 0, and the proteasome inhibitor is a dipeptide or psuedopeptide analog. In some embodiments, the proteasome is a dipeptide or psuedopeptide analog wherein $R_1$ is the side chain of norleucine or phenylalanine and $R_4$ is selected from the side chains of leucine, phenylalanine, homophenylalanine, and alanine. In some embodiments, $R_1$ is the side chain of phenylalanine and $R_4$ is the side chain of leucine, phenylalanine or homophenylalanine. In some embodiments, $R_1$ is the side chain of norleucine and $R_4$ is the side chain of phenylalanine, homophenylalanine and alanine.

In some embodiments, m is 0 and n is 1 and the proteasome inhibitor is a tripeptide or pseudopeptide analog. In some embodiments, the proteasome inhibitor is a tripeptide or pseudopeptide analog and $R_1$ is the side chain of phenylalanine, $R_2$ is the side chain of leucine or phenylalanine, and $R_4$ is the side chain of leucine or glycine.

In some embodiments, n and m are each 1 and the proteasome inhibitor is a tetrapeptide or pseudopeptide analog. In some embodiments, the proteasome inhibitor is a tetrapeptide analog and $R_1$ is the side chain of phenylalanine, $R_2$ is selected from the side chains of alanine and phenylalanine, $R_3$ together with $Q_3$ forms the side chain of proline, and $R_4$ is the side chain of glycine.

In some embodiments, $A_1$, $A_2$ and $A_3$ each comprise an amide group (i.e., a peptide bond) and the proteasome inhibitor is a compound of formula (II):

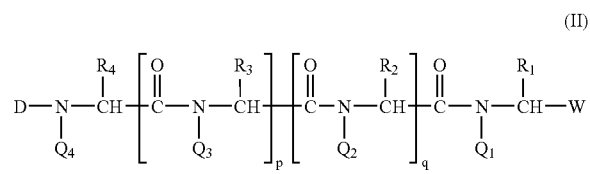

wherein:
p is an integer from 0 to 1;
q is an integer from 0 to 1;
D is selected from the group consisting of H, alkyl, branched alkyl, aralkyl, aryl, acyl, aroyl, alkoxycarbonyl, aralkyloxycarbonyl and aryloxycarbonyl;
$Q_1$, $Q_2$, $Q_3$, and $Q_4$ are independently selected from H and alkyl;
$R_1$, $R_2$, $R_3$, and $R_4$ are independently selected from H, alkyl, branched alkyl, aryl, aralkyl, and substituted alkyl; or
one or more of $R_2$ and $Q_2$ together, $R_3$ and $Q_3$ together and $R_4$ and $Q_4$ together are $C_2$-$C_5$ alkylene; and
W is selected from the group consisting of:

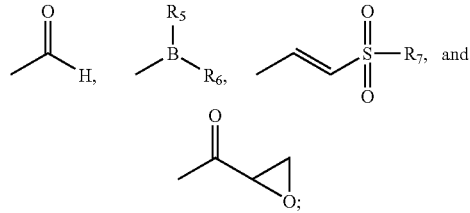

wherein:
$R_5$ and $R_6$ are independently selected from hydroxy, alkoxy, aralkoxy, and aryloxy, or $R_5$ and $R_6$ together form a di-oxyalkylene group having two oxy radicals separated by at least two connecting atoms in a chain or ring, said chain or ring comprising carbon atoms and optionally a heteroatom or heteroatoms, N, S, or O; and
$R_7$ is selected from alkyl, aryl, and substituted aryl; or
a pharmaceutically acceptable salt thereof.

In some embodiments, $R_1$ is selected from the group consisting of alkyl, branched alkyl, and aralkyl. In some embodiments, $R_1$ is n-butyl or benzyl.

In some embodiments, D is selected from Boc, Fmoc, Ac, and Cbz.

In some embodiments, W is aldehyde (CHO).

In some embodiments, p and q are each 0, $R_1$ is selected from benzyl and n-butyl, and $R_4$ is selected from benzyl, isobutyl, methyl and phenylethyl. In some embodiments, $R_1$ is n-butyl and $R_4$ is selected from benzyl, methyl, and phenylethyl.

In some embodiments, p and q are each 1, $R_1$ is benzyl or n-butyl, $R_2$ is methyl or benzyl, $R_3$ and $Q_3$ together are $C_3$ alkylene, and $R_4$ is H.

In some embodiments, q is 1 and p is 0, $R_1$ is benzyl of n-butyl, $R_2$ is isobutyl or benzyl, and $R_4$ is isobutyl or H.

In some embodiments, the compound is selected from the group consisting of:

N-carbobenzyloxy-leucyl-norleucinal (Cbz-LnL-CHO),

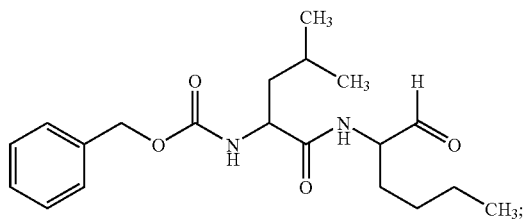

N-carbobenzyloxy-phenylalanyl-phenylalanylal (Cbz-FF-CHO),

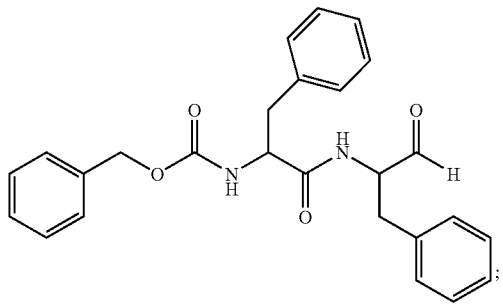

N-carbobenzyloxy-homophenylalanyl-phenylalanylal (Cbz-hFF-CHO),

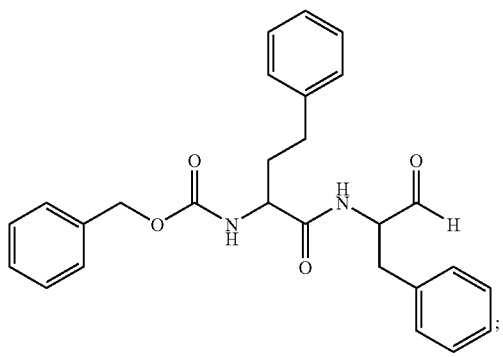

N-carbobenzyloxy-leucyl-phenylalanylal (Cbz-LF-CHO),

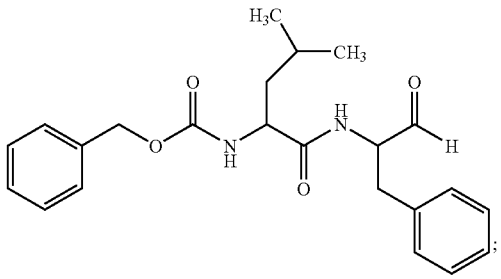

N-carbobenzyloxy-alanyl-phenylalanylal (Cbz-AF-CHO),

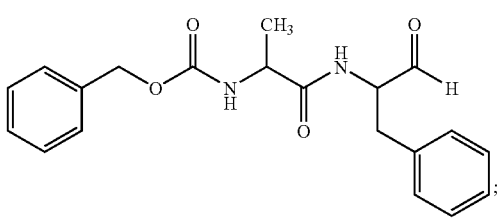

N-carbobenzyloxy-glycyl-prolyl-alanyl-phenylalanylal (Cbz-GPAF-CHO),

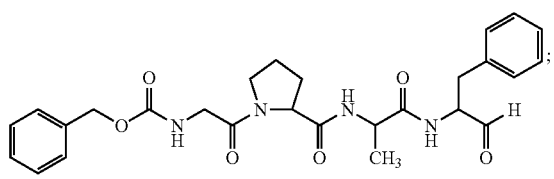

N-carbobenzyloxy-glycyl-prolyl-phenylalanyl-phenylalanylal (Cbz-GPFF-CHO)

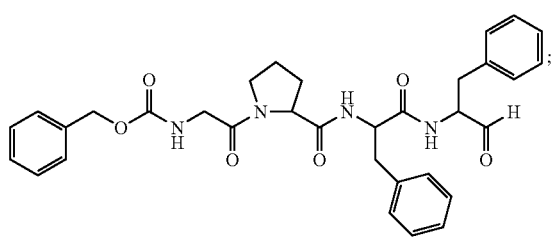

N-carbobenzyloxy-leucyl-leucyl-phenylalanylal (Cbz-LLF-CHO),

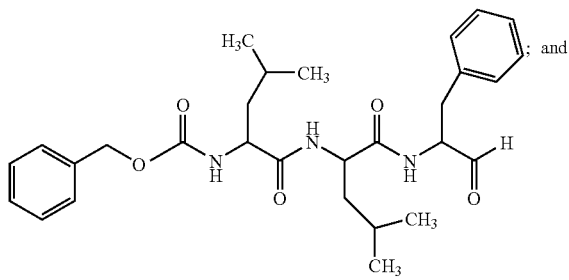

N-carbobenzyloxy-glycyl-phenylalanyl-phenylalanylal (Cbz-GFF-CHO),

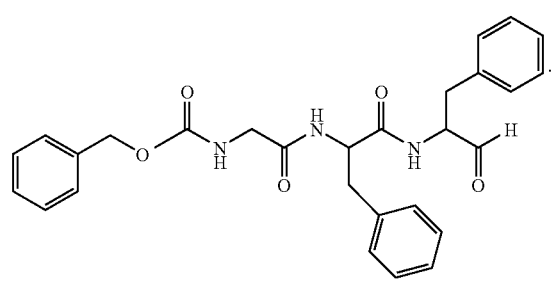

In some embodiments, W is a boronic acid or a boronic ester. In some embodiments, the compound is selected from the group consisting of:

N-carbobenzyloxy-leucyl-norleucine boronic acid (Cbz-LnL-BA),

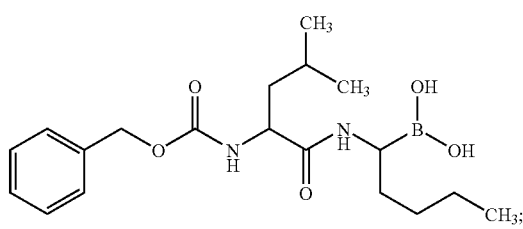

N-carbobenzyloxy-phenylalanyl-phenylalanine boronic acid (Cbz-FF-BA),

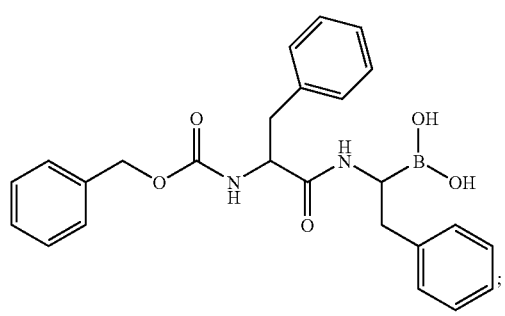

N-carbobenzyloxy-homophenylalanyl-phenylalanine boronic acid (Cbz-hFF-BA),

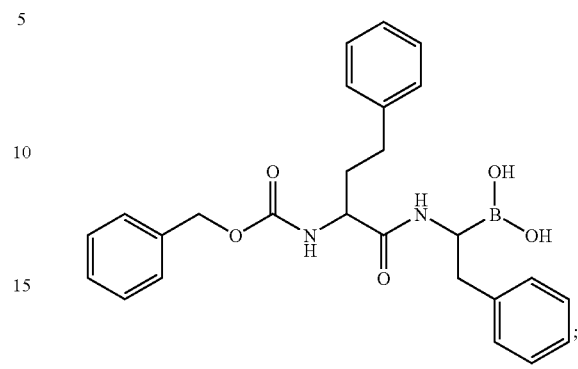

N-carbobenzyloxy-leucyl-phenylalanine boronic acid (Cbz-LF-BA),

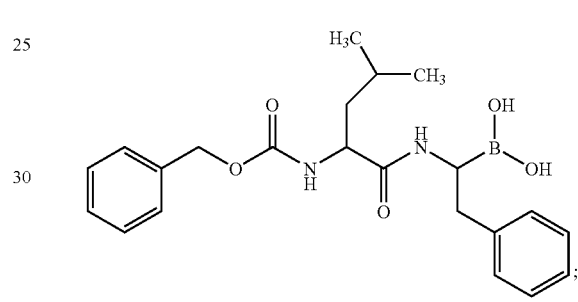

N-carbobenzyloxy-alanyl-phenylalanine boronic acid (Cbz-AF-BA),

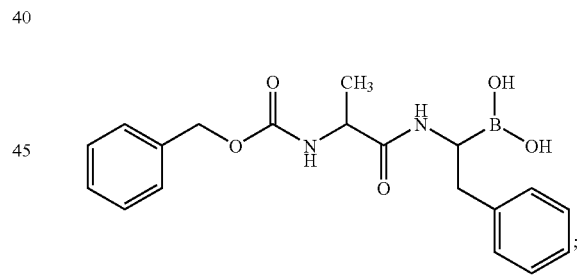

N-carbobenzyloxy-glycyl-prolyl-alanyl-phenylalanine boronic acid (Cbz-GPAF-BA),

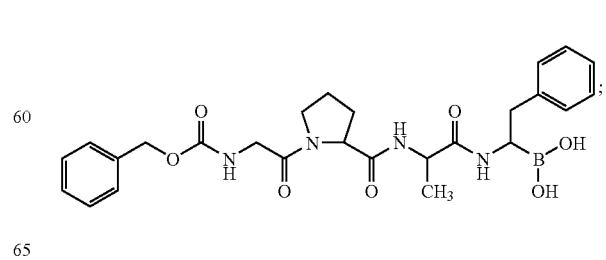

N-carbobenzyloxy-glycyl-prolyl-phenylalanyl-phenylalanine boronic acid (Cbz-GPFF-BA),

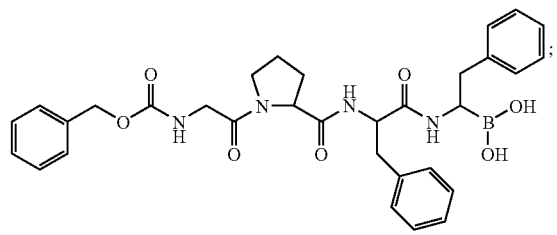

N-carbobenzyloxy-leucyl-leucyl-phenylalanine boronic acid (Cbz-LLF-BA),

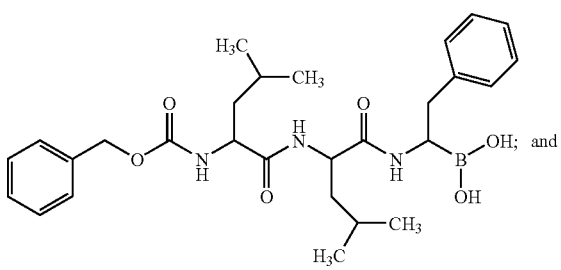

N-carbobenzyloxy-glycyl-phenylalanyl-phenylalanine boronic acid (Cbz-GFF-BA),

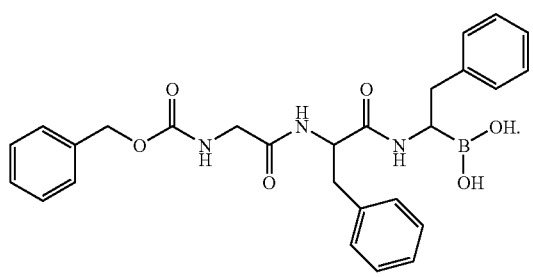

In some embodiments, W is a vinyl sulfone. In some embodiments, the vinyl sulfone is a methyl vinyl sulfone (i.e., $R_7$ is methyl). In some embodiments, the vinyl sulfone is a phenolic vinyl sulfone (i.e., $R_7$ is —$C_6H_5OH$). In some embodiments, the compound is selected from the group consisting of:

N-carbobenzyloxy-leucyl-norleucine methyl vinyl sulfone (Cbz-LnL-mVS),

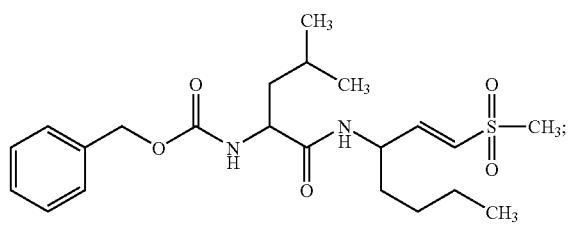

N-carbobenzyloxy-phenylalanyl-phenylalanine methyl vinyl sulfone (Cbz-FF-mVS),

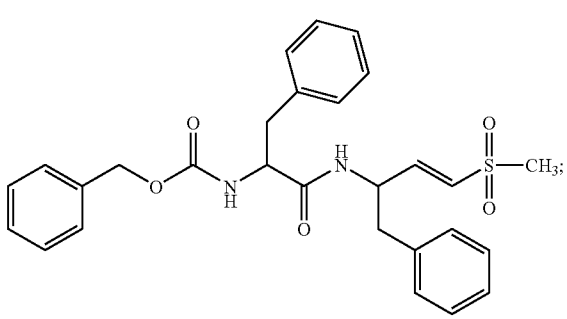

N-carbobenzyloxy-homophenylalanyl-phenylalanine methyl vinyl sulfone (Cbz-hFF-mVS),

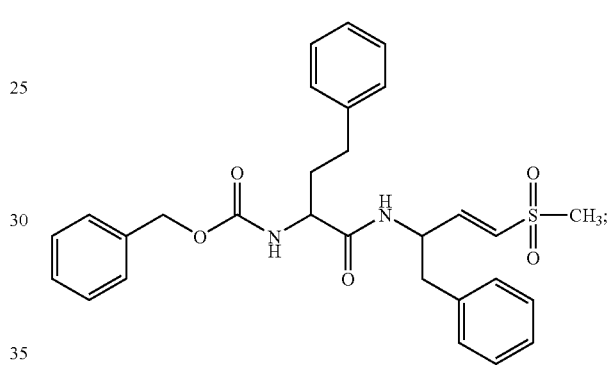

N-carbobenzyloxy-leucyl-phenylalanine methyl vinyl sulfone (Cbz-LF-mVS),

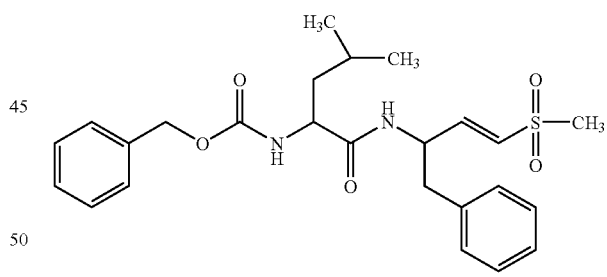

N-carbobenzyloxy-alanyl-phenylalanine methyl vinyl sulfone (Cbz-AF-mVS),

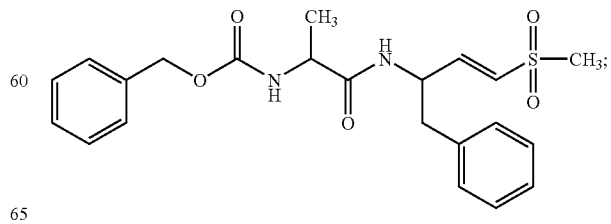

N-carbobenzyloxy-glycyl-prolyl-alanyl-phenylalanine methyl vinyl sulfone (Cbz-GPAF-mVS),

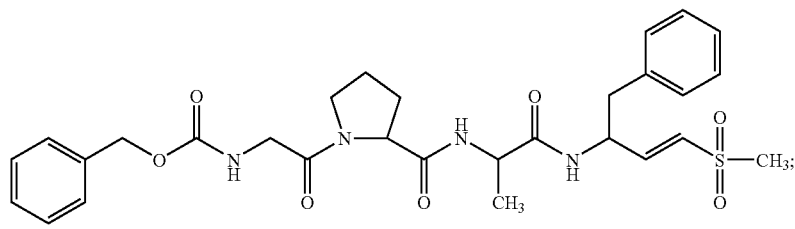

N-carbobenzyloxy-glycyl-prolyl-phenylalanyl-phenylalanine methyl vinyl sulfone (Cbz-GPFF-mVS),

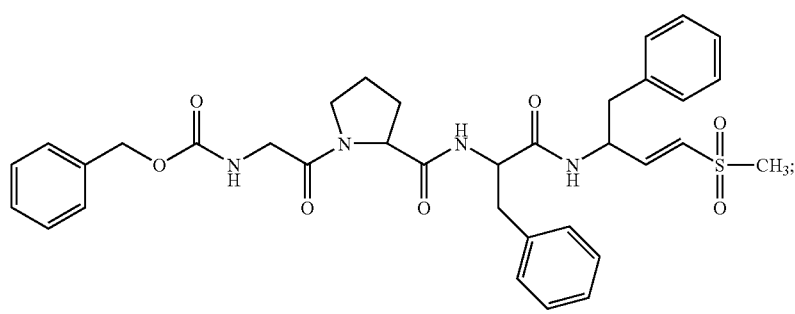

N-carbobenzyloxy-leucyl-leucyl-phenylalanine methyl vinyl sulfone (Cbz-LLF-mVS),

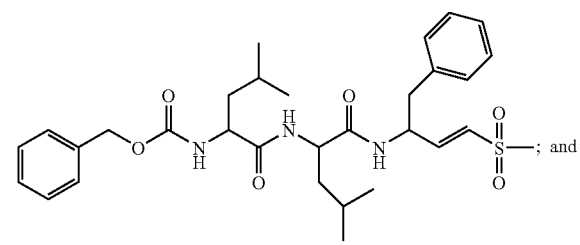

N-carbobenzyloxy-glycyl-phenylalanyl-phenylalanine methyl vinyl sulfone (Cbz-GFF-mVS),

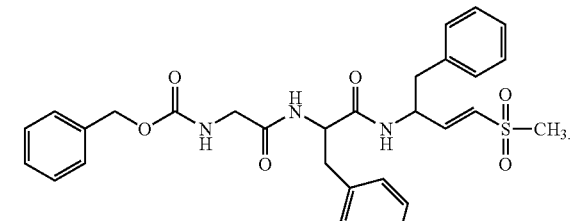

N-carbobenzyloxy-leucyl-norleucine epoxy ketone (Cbz-LnL-EK),

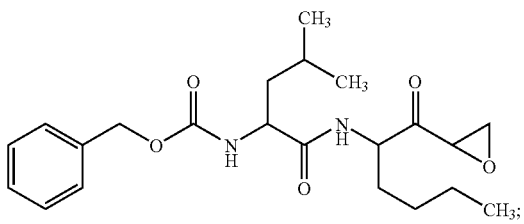

N-carbobenzyloxy-phenylalanyl-phenylalanine epoxy ketone (Cbz-FF-EK),

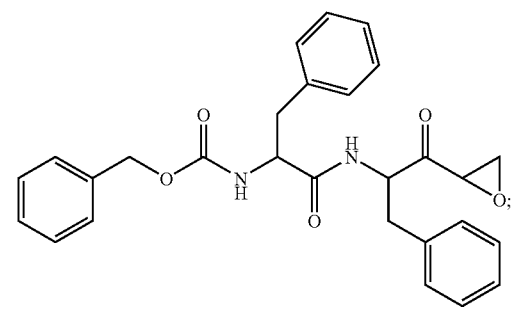

In some embodiments, W is an epoxy ketone. In some embodiments, the compound is selected from the group consisting of:

N-carbobenzyloxy-homophenylalanyl-phenylalanine epoxy ketone (Cbz-hFF-EK),

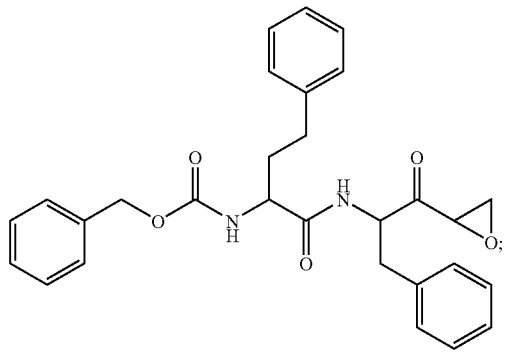

N-carbobenzyloxy-leucyl-phenylalanine epoxy ketone (Cbz-LF-EK),

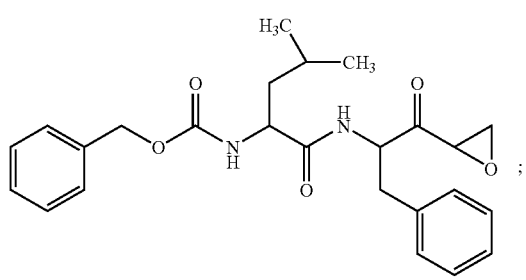

N-carbobenzyloxy-alanyl-phenylalanine epoxy ketone (Cbz-AF-EK),

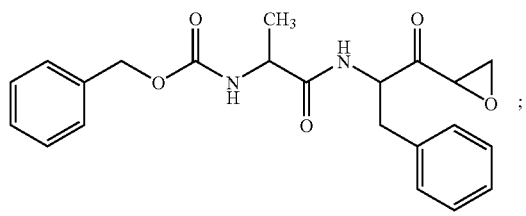

N-carbobenzyloxy-glycyl-prolyl-alanyl-phenylalanine epoxy ketone (Cbz-GPAF-EK),

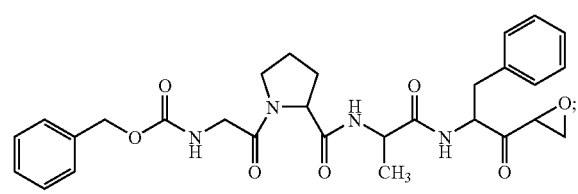

N-carbobenzyloxy-glycyl-prolyl-phenylalanyl-phenylalanine epoxy ketone (Cbz-GPFF-EK),

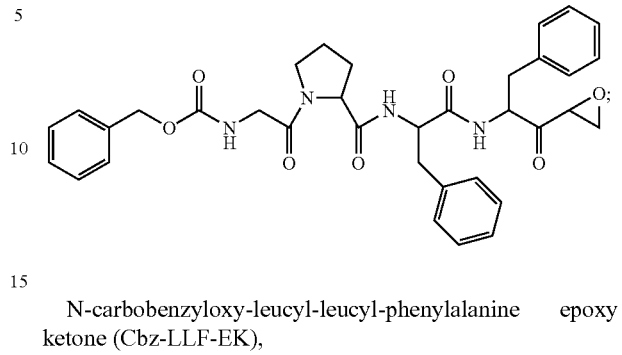

N-carbobenzyloxy-leucyl-leucyl-phenylalanine epoxy ketone (Cbz-LLF-EK),

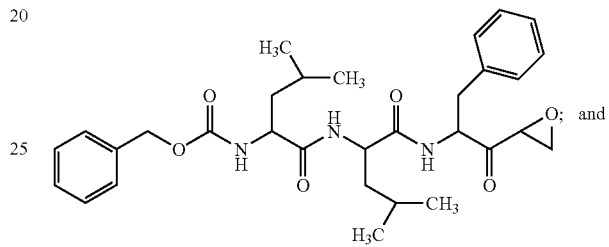

N-carbobenzyloxy-glycyl-phenylalanyl-phenylalanine epoxy ketone (Cbz-GFF-EK),

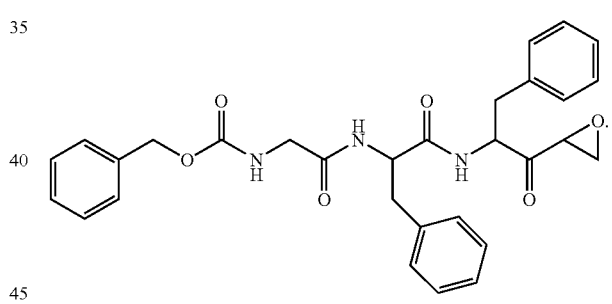

In some embodiments, the compound of Formula (I-II) has a greater than 25-fold preference for inhibiting the immunoproteasome as compared to the constitutive proteasome. In some embodiments, the compound of Formula (I-II) has a greater than 50-fold preference for inhibiting the immunoproteasome as compared to the constitutive proteasome, and in some embodiments, the compound of Formula (I-II) has a greater than 100-fold preference for inhibiting the immunoproteasome as compared to the constitutive proteasome.

In some embodiments, the preference of an inhibitor for the immunoproteasome as compared to the constitutive proteasome can be determined by evaluating either or both the chymotrypsin-like (ChT-L) and branched chain amino acid preferring (BrAAP) activities of the two proteasomes (i.e., the immunoproteasome and the constitutive proteasome). In some embodiments, the immunoproteasome is from spleen tissue. In some embodiments, the constitutive proteasome is from pituitary tissue. A compound having a greater preference for the immunoproteasome as compared to the constitutive proteasome can, for example, have a smaller $K_i$ or a smaller $IC_{50}$ concentration for an immunoproteasome than for a constitutive proteasome.

In some embodiments, the compound of Formula (I-II) has a $K_i$ of 25 µM or less for the immunoproteasome. In some embodiments, the $K_i$ of a compound of Formula (I-II) can be determined by measuring the amount of the compound of Formula (I-II) that, when pre-incubated with the immunoproteasome, inhibits the immunoproteasome from catalyzing the hydrolysis of a known substrate of the immunoproteasome. In some embodiments, the immunoproteasome is a proteasome from spleen tissue and the known substrate is one of CBZ-GPALG-para-amino-benzoate (pAB) and CBZ-GGF-pAB. In some embodiments, CBZ-GPALG-pAB is the known substrate for the BrAAP activity of spleen immunoproteasome and CBZ-GGF-pAB is the known substrate for the ChT-L activity of spleen immunoproteasome.

In some embodiments, the compound that has a $K_i$ value of 25 µM or less for the immunoproteasome has a $K_i$ value of 10 µM or less for the immunoproteasome. In some embodiments, the compound has a $K_i$ value of 5 µM or less for the immunoproteasome.

III. Pharmaceutical Formulations

The compounds of Formula (I-II) and the pharmaceutically acceptable salts thereof are all referred to herein as "active compounds." Pharmaceutical formulations comprising the aforementioned active compounds are provided herein. These pharmaceutical formulations comprise active compounds as described herein, in a pharmaceutically acceptable carrier. Pharmaceutical formulations can be prepared for oral, intravenous, or aerosol administration as discussed in greater detail below. Also, the presently disclosed subject matter provides such active compounds that have been lyophilized and that can be reconstituted to form pharmaceutically acceptable formulations for administration, for example, as by intravenous or intramuscular injection.

Pharmaceutically acceptable salts include the gluconate, lactate, acetate, tartarate, citrate, phosphate, maleate, borate, nitrate, sulfate, and hydrochloride salts.

The therapeutically effective dosage of any specific active compound, the use of which is within the scope of embodiments described herein, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level can restrict intravenous dosages to a lower level, such as up to about 10 mg/kg, with all weights being calculated based on the weight of the active base, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Preferred dosages are 1 µmol/kg to 50 µmol/kg, and more preferably 22 µmol/kg and 33 µmol/kg of the compound for intravenous or oral administration. The duration of the treatment is usually once per day for a period of two to three weeks or until the condition is essentially controlled. Lower doses given less frequently can be used prophylactically to prevent or reduce the incidence of recurrence of a disease or to pre-emptively treat a subject at high risk of developing a disease treatable by inhibiting the immunoproteasome.

In accordance with the presently disclosed methods, pharmaceutically active compounds as described herein can be administered orally as a solid or as a liquid, or can be administered intramuscularly or intravenously as a solution, suspension, or emulsion. Alternatively, the compounds or salts also can be administered by inhalation, intravenously, or intramuscularly as a liposomal suspension. When administered through inhalation the active compound or salt should be in the form of a plurality of solid particles or droplets having a particle size from about 0.5 to about 5 microns, and preferably from about 1 to about 2 microns.

Pharmaceutical formulations suitable for intravenous or intramuscular injection are further embodiments provided herein. The pharmaceutical formulations can comprise a compound of Formula (I-II) described herein, or a pharmaceutically acceptable salt thereof, in any pharmaceutically acceptable carrier. If a solution is desired, water is the carrier of choice with respect to water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and typically by filtration through a 0.22-micron filter. Subsequent to sterilization, the solution can be dispensed into appropriate receptacles, such as depyrogenated glass vials. The dispensing is preferably done by an aseptic method. Sterilized closures can then be placed on the vials and, if desired, the vial contents can be lyophilized.

In addition to compounds of Formula (I-II) or their salts, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. The antimicrobial preservative is typically employed when the formulation is placed in a vial designed for multi-dose use. The pharmaceutical formulations described herein can be lyophilized using techniques well known in the art. In some embodiments, a compound of Formula (I-II) can be administered in combination with one or more compounds that protect the compound of Formula (I-II) from enzymatic degradation, e.g., protease and peptidase inhibitors such as alpha-1 antiprotease, captropril, thiorphan, and the HIV protease inhibitors, and the like.

In yet another embodiment of the subject matter described herein, there is provided an injectable, stable, sterile formulation comprising a compound of Formula (I-II), or a salt thereof, in a unit dosage form in a sealed container. The compound or salt is provided in the form of a lyophilizate, which is capable of being reconstituted with a suitable pharmaceutically acceptable carrier to form a liquid formulation suitable for injection thereof into a subject. The unit dosage form typically comprises from about 10 mg to about 10 grams of the compound salt. When the compound or salt is substantially water-insoluble, a sufficient amount of emulsifying agent, which is physiologically acceptable, can be employed in sufficient quantity to emulsify the compound or salt in an aqueous carrier. One such useful emulsifying agent is phosphatidyl choline.

Other pharmaceutical formulations can be prepared from the water-insoluble compounds disclosed herein, or salts thereof, such as aqueous base emulsions. In such an instance, the formulation will contain a sufficient amount of pharmaceutically acceptable emulsifying agent to emulsify the desired amount of the compound or salt thereof. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound will be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques.

The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol by inhalation. These formulations comprise a solution or suspension of a desired compound described herein or a salt thereof, or a plurality of solid particles of the compound or salt. The desired formulation can be placed in a small chamber and nebulized. Nebulization can be accomplished by compressed air or by ultrasonic energy to form a plurality of liquid droplets or solid particles comprising the compounds or salts. The liquid droplets or solid particles should have a particle size in the range of about 0.5 to about 10 microns, more preferably from about 0.5 to about 5 microns. The solid particles can be obtained by processing the solid compound or a salt thereof, in any appropriate manner known in the art, such as by micronization. Most preferably, the size of the solid particles or droplets will be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

When the pharmaceutical formulation suitable for administration as an aerosol is in the form of a liquid, the formulation can comprise a water-soluble active compound in a carrier that comprises water. A surfactant can be present, which lowers the surface tension of the formulation sufficiently to result in the formation of droplets within the desired size range when subjected to nebulization.

As indicated, both water-soluble and water-insoluble active compounds are provided. As used herein, the term "water-soluble" is meant to define any composition that is soluble in water in an amount of about 50 mg/mL, or greater. Also, as used herein, the term "water-insoluble" is meant to define any composition that has a solubility in water of less than about 20 mg/mL. In some embodiments, water-soluble compounds or salts can be desirable whereas in other embodiments water-insoluble compounds or salts likewise can be desirable.

IV. Methods for Treating Diseases with Immunoproteasome Inhibitors

IV.A. Methods of Inhibiting the Immunoproteasome

The presently disclosed subject matter provides methods and compositions for inhibiting the immunoproteasome. In some embodiments, these methods comprise contacting a cell with a compound of Formula (I-II). In some embodiments, the cell is in a subject The subject treated in the presently disclosed subject matter in its many embodiments is desirably a human subject, although it is to be understood the methods described herein are effective with respect to all vertebrate species, which are intended to be included in the term "subject." In some embodiments the subject is warm-blooded vertebrate. Thus, the methods described herein can be used as treatment for mammals and birds.

More particularly, provided herein is the treatment of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided herein is the treatment of birds, including the treatment of those kinds of birds that are endangered, kept in zoos and as pets, as well as fowl, and more particularly domesticated fowl, i.e., poultry, such as turkeys, chickens, ducks, geese, guinea fowl, and the like, as they also are of economical importance to humans. Thus, embodiments of the methods described herein include the treatment of livestock, including, but not limited to, domesticated swine (pigs and hogs), ruminants, horses, poultry, and the like.

IV.B. Methods of Treating Cancer

The presently disclosed compounds have been shown to preferentially cause the death of cancer cells expressing the immunoproteasome subunits, while sparing other cells that express only constitutive proteasome subunits. Thus, the presently disclosed subject matter provides methods and compositions for inhibiting cell proliferation through selectively inhibiting the immunoproteasome. In some embodiments, the presently disclosed subject matter provides a method for treating a cancer in a subject in need of treatment thereof, the method comprising administering a compound having specificity for the immunoproteasome (i.e., an immunoproteasome inhibitor). In some embodiments, the proteasome inhibitor is a compound of Formula (I-II).

By the term "treatment of cancer" or "treating cancer" is intended description of an activity of compounds of the presently disclosed subject matter wherein said activity prevents, alleviates or ameliorates any of the specific phenomena known in the art to be associated with the pathology commonly known as "cancer." The term "cancer" refers to the spectrum of pathological symptoms associated with the initiation or progression, as well as metastasis, of malignant tumors. By the term "tumor" is intended a growth of tissue in which the multiplication of cells is uncontrolled and progressive. A tumor that is particularly relevant is a malignant tumor, one in which the primary tumor has the properties of invasion or metastasis or which shows a greater degree of anaplasia than do benign tumors.

An "effective amount" is defined herein in relation to the treatment of cancers is an amount that will decrease, reduce, inhibit, or otherwise abrogate the growth of a cancer cell or tumor.

Thus, "treatment of cancer" or "treating a cancer" refers to an activity that prevents, alleviates or ameliorates any of the primary phenomena (initiation, progression, metastasis) or secondary symptoms associated with the disease. Cancers that are treatable are broadly divided into the categories of carcinoma, lymphoma and sarcoma. Examples of carcinomas that can be treated by the compound of Formula (I-II) include, but are not limited to: adenocarcinoma, acinic cell adenocarcinoma, adrenal cortical carcinomas, alveoli cell carcinoma, anaplastic carcinoma, basaloid carcinoma, basal cell carcinoma, bronchiolar carcinoma, bronchogenic carcinoma, renaladinol carcinoma, embryonal carcinoma, anometroid carcinoma, fibrolamolar liver cell carcinoma, follicular carcinomas, giant cell carcinomas, hepatocellular carcinoma, intraepidermal carcinoma, intraepithelial carcinoma, leptomanigio carcinoma, medullary carcinoma, melanotic carcinoma, menigual carcinoma, mesometonephric carcinoma, oat cell carcinoma, squamal cell carcinoma, sweat gland carcinoma, transitional cell carcinoma, and tubular cell carcinoma. Sarcomas that can be treated by the compounds of Formula (I-II) include, but are not limited to: amelioblastic sarcoma, angiolithic sarcoma, botryoid sarcoma, endometrial stroma sarcoma, ewing sarcoma, fascicular sarcoma, giant cell sarcoma, granulositic sarcoma, immunoblastic sarcoma, juxaccordial osteogenic sarcoma, coppices sarcoma, leukocytic sarcoma (leukemia), lymphatic sarcoma (lympho sarcoma), medullary sarcoma, myeloid sarcoma (granulocitic sarcoma), austiogenci sarcoma, periosteal sarcoma, reticulum cell sarcoma (histiocytic lymphoma), round cell sarcoma, spindle cell sarcoma, synovial sarcoma, and telangiectatic audiogenic sarcoma. Lymphomas that can be treated by the compounds of Formula (I-II) include, but are not limited to: Hodgkin's disease and lymphocytic lymphomas, such as Burkitt's lymphoma, NPDL, NML, NH and diffuse lymphomas.

In some embodiments, the tumor or cancer is present in a hemopoietic cell. In some embodiments, the tumor or cancer is multiple myeloma. As used herein, the term "multiple myeloma" refers to a malignancy of the bone marrow in which cancerous plasma cells grow out of control and create a tumor. When these tumors grow in multiple sites, they are referred to as multiple myeloma. Normally, plasma cells make up less than five percent of the cells in bone marrow, but people with multiple myeloma have anywhere from ten percent to more than ninety percent. The overgrowth of malignant plasma cells in bone marrow can cause a number of serious problems throughout the body. Over time, the abnormal cells can permeate the interior of the bone and erode the bone cortex (outer layer). These weakened bones are more susceptible to bone fractures, especially in the spine, skull, ribs, and pelvis.

Amounts and regimens for the administration of immunoproteasome inhibitors can be determined readily by those with ordinary skill in the clinical art of treating cancer-related disorders such as the primary phenomena (initiation, progression, metastasis) or secondary symptoms associated with the disease. Generally, the dosage will vary depending upon considerations such as: type of composition employed; age; health; medical conditions being treated; kind of concurrent treatment, if any, frequency of treatment and the nature of the effect desired; extent of tissue damage; gender; duration of the symptoms; and, counter indications, if any, and other variables to be adjusted by the individual physician. A desired dosage can be administered in one or more applications to obtain the desired results. Pharmaceutical compositions containing the immunoproteasome inhibitors of the presently disclosed subject matter can be provided in unit dosage forms.

Immunoproteasome inhibitors of the presently disclosed subject matter also can be used as part of a combination treatment for a cancer. Thus, the immunoproteasome inhibitors described herein can be used in combination with another cancer treatment, for example, surgery, radiation or administration of one or more additional neoplastic agents. In some embodiments, both the immunoproteasome inhibitor and the additional neoplastic agent or agents are intended to inhibit the proliferation of tumor cells. Alternatively, administration of an immunoproteasome inhibitor can provide a method for augmenting the expression of p53 in normal cells, thereby allowing for repair of DNA damaged by cytotoxic neoplastic agents and reducing the sensitivity of normal cells to higher doses of radiation or cytotoxic drugs. Administration of imunoproteasome inhibitors, therefore, would be a means of permitting exposure of tumors to higher doses of radiation or anti-cancer agents, enhancing the eradication of the tumor.

Thus, a variety of chemical compounds, also described as "antineoplastic" agents or "chemotherapeutic agents" can be used in combination with one or more of the immunoproteasome inhibitors of the presently described subject matter. Such compounds include, but are not limited to, alkylating agents, DNA intercalators, antimicrotubule agents, anti-metabolites, protein synthesis inhibitors, inhibitors of DNA or RNA synthesis, DNA base analogs, topoisomerase inhibitors, anti-angiogenesis agents, and telomerase inhibitors or telomeric DNA binding compounds. For example, suitable alkylating agents include alkyl sulfonates, such as busulfan, improsulfan, and piposulfan; aziridines, such as a benzodizepa, carboquone, meturedepa, and uredepa; ethylenimines and methylmelamines, such as altretamine, triethylenemelamine, triethylenephosphoramide, triethylenethiophosphoramide, and trimethylolmelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine, and ranimustine.

Antibiotics used in the treatment of cancer include dactinomycin, daunorubicin, doxorubicin, idarubicin, bleomycin sulfate, mytomycin, plicamycin, and streptozocin. Chemotherapeutic antimetabolites include mercaptopurine, thioguanine, cladribine, fludarabine phosphate, fluorouracil (5-FU), floxuridine, cytarabine, pentostatin, methotrexate, and azathioprine, acyclovir, adenine $\beta$-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine $\beta$-1-D-arabinoside, diazooxynorleucine, dideoxynucleosides, 5-fluorodeoxycytidine, 5-fluorodeoxyuridine, and hydroxyurea.

Chemotherapeutic protein synthesis inhibitors include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim. Inhibitors of DNA synthesis, including alkylating agents such as dimethyl sulfate, mitomycin C, nitrogen and sulfur mustards, intercalating agents, such as acridine dyes, actinomycins, adriamycin, anthracenes, benzopyrene, ethidium bromide, propidium diiodide-intertwining, and agents, such as distamycin and netropsin, also can be combined with compounds of Formula (I-II) in pharmaceutical compositions. Topoisomerase inhibitors, such as coumermycin, nalidixic acid, novobiocin, and oxolinic acid, inhibitors of cell division, including colcemide, colchicine, vinblastine, and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin, and streptolydigin also can be combined with the proteasome inhibitor compounds of the presently disclosed subject matter to provide a suitable cancer treatment.

Thus, current chemotherapeutic agents that can be used in a combination treatment with a proteasome inhibitor of the presently disclosed subject matter include, adrimycin, 5-fluorouracil (5FU), etoposide, camptothecin, actinomycin-D, mitomycin, cisplatin, hydrogen peroxide, carboplatin, procarbazine, mechlorethamine, cyclophosphamide, ifosfamide, melphalan, chjlorambucil, bisulfan, nitrosurea, dactinomycin, duanorubicin, doxorubicin, bleomycin, plicomycin, tamoxifen, taxol, transplatimun, vinblastin, and methotrexate, and the like.

Combination treatments involving an immunoproteasome inhibitor compound and another therapeutic agent, such as another chemotherapeutic agent, can be achieved by contacting cells with the immunoproteasome inhibitor and the other agent at the same time. Such combination treatments can be achieved by contacting the cell with a single composition or pharmacological formulation that includes both agents, or by contacting the cell with two distinct compositions or formulations, at the same time, wherein one composition includes the immunoproteasome inhibitor and the other includes the other agent.

Alternatively, administration of the immunoproteasome inhibitor can precede or follow treatment with the other agent by intervals ranging from minutes to weeks. In embodiments where the other agent and the immunoproteasome inhibitor are applied separately to the cell, one would generally ensure that a significant period of time did not expire between the time of each delivery, such that the other agent and the immunoproteasome inhibitor would still be able to exert an advantageously combined effect on the cell. In such instances, it is provided that one would contact the cell with both modalities within about 12-24 hours of each other and, optionally, within about 6-12 hours of each other. In some situations, it can be desirable to extend the time period for treatment significantly, however, where several days (2, 3, 4, 5, 6 or 7) to several weeks (1, 2, 3, 4, 5, 6, 7 or 8) lapse between the respective administrations. Also, under some circumstances, more than one administration of either the immunoproteasome inhibitor or of the other agent will be desired.

In another embodiment, an immunoproteasome inhibitor of the presently disclosed subject matter is combined with a cytotoxic agent bound to a targeting agent, such as a monoclonal antibody (e.g., a murine or humanized monoclonal antibody). It will be appreciated that the use of a targeting agent can allow the introduction of cytotoxic agents into cancer cells with greater specificity. Thus, the active form of the cytotoxic agent (i.e., the free form) will be present only in cells targeted by the antibody.

Additional cancer treatments also can be used in combination with administration of an immunoproteasome inhibitor. For example, an immunoproteasome inhibitor compound of the presently disclosed subject matter can be used as part of a treatment course further involving attempts to surgically remove part or all of a cancerous growth. For instance, an immunoproteasome inhibitor of the presently disclosed subject matter can be administered after surgical treatment of a subject to treat any remaining neoplastic or metastasized cells. Treatment with an immunoproteasome inhibitor of the presently disclosed subject matter also can precede surgery, in an effort to shrink the size of a tumor to reduce the amount of tissue to be excised, thereby making the surgery less invasive and traumatic.

Treating cancer with an immunoproteasome inhibitor of the presently disclosed subject matter can further include one or more treatment courses with a radiotherapeutic agent to induce DNA damage. Radiotherapeutic agents, include, for example, gamma irradiation, X-rays, UV-irradiation, microwaves, electronic emissions, radioisotopes, and the like. Therapy can be achieved by irradiating the localized tumor site with the above-described forms of radiation.

A combination therapy also can involve immunotherapy directed at tumor antigen markers that are found on the surface of tumor cells. Treatment of a cancer with an immunoproteasome inhibitor of the presently disclosed subject matter can further be combined with a gene therapy based treatment, targeted towards oncogenes and/or cell cycle controlling genes, such as p53, p16, p21, Rb, APC, DCC, NF-1, NF-2, BRCA2, FHIT, WT-1, MEN-I, MEN-II, BRCA1, VHL, FCC, MCC, ras, myc, neu, raf, erb, src, fms, jun, trk, ret, gsp, hst, bcl, and abl, which are often mutated versions of their normal cellular counterparts in cancerous tissues.

The immunoproteasome inhibitors of the presently disclosed subject matter can be tested to measure their ability to inhibit growth of cancer cells, to induce cytotoxic events in cancer cells, to induce apoptosis of the cancer cells, to reduce tumor burden, and to inhibit metastases. For example, one can measure cell growth according to the MTT assay. Growth assays as measured by the MTT assay are well known in the art. In the MTT assay, cells are incubated with various concentrations of anti-cancer compound, and cell viability is determined by monitoring the formation of a colored formazan salt of the tetrazolium salt, 3-(4,5-dimethylthiazol-2-yl)-2,5-diphenyltetrazolium bromide (MTT). Other known assays for measuring cell death also can be employed.

In vivo testing can be performed using a mouse xenograft model, for example, in which tumor cells are grafted onto nude mice, in which mice treated with a compound of Formula (I-II) are expected to have tumor masses that, on average, increase for a period following initial dosing, but will shrink in mass with continuing treatment. In contrast, mice treated with a control (e.g., DMSO) are expected to have tumor masses that continue to increase.

The methods disclosed herein also can be used to treat other cell proliferative diseases, such as psoriasis or restenosis.

IV.C. Methods of Treating Inflammation

In some embodiments, the immunoproteasome inhibitors of the presently disclosed subject matter can be used to treat inflammation. Thus, the compounds of Formula (I-II) can be used to treat chronic or acute inflammation that is the result of transplantation rejection, local infections, arthritis, rheumatoid arthritis, dermatosis, inflammatory bowel disease, asthma, osteoporosis, osteoarthritis and autoimmune diseases. The immunoproteasome inhibitors of the presently disclosed subject matter can be employed to prevent the rejection or inflammation of transplanted tissue or organs of any type, for example, heart, lung, kidney, liver, skin grafts, and tissue grafts. Additionally, inflammation associated with psoriasis and restenosis can be treated.

The term "treatment of inflammation" or "treating inflammation" is intended to include the administration of compounds of the presently disclosed subject matter to a subject for purposes which can include prophylaxis, amelioration, prevention or cure of an inflammatory response. Such treatment need not necessarily completely ameliorate the inflammatory response. Further, such treatment can be used in conjunction with other traditional treatments for reducing the inflammatory condition known to those of skill in the art. Additionally, the immunoproteasome inhibitors can be provided as a "preventive" treatment before detection of an inflammatory state, so as to prevent the inflammation from developing in patients at high risk for inflammation, such as, for example, transplant patients.

In some embodiments, efficacious levels of the immunoproteasome inhibitors are administered so as to provide therapeutic benefits against the harmful secondary effects of inflammation. By an "efficacious level" of a compound is meant a level at which some relief is afforded to the patient who is the recipient of the treatment. By an "abnormal" host inflammatory condition is meant a level of inflammation in the subject at a site that exceeds the norm for the healthy medical state of the subject, or exceeds a desired level. By "secondary" tissue damage or toxic effects is meant the tissue damage or toxic effects which occur to otherwise healthy tissues, organs, and the cells therein, due to the presence of an inflammatory response, including as a result of a "primary" inflammatory response elsewhere in the body.

Amounts and regimens for the administration of immunoproteasome inhibitors can be determined readily by those with ordinary skill in the clinical art of treating inflammation-related disorders such as arthritis, tissue injury and tissue rejection. Generally, the dosage will vary depending upon considerations such as: type of pharmaceutical composition employed; age; health; medical conditions being treated; kind of concurrent treatment, if any, frequency of treatment and the nature of the effect desired; extent of tissue damage; gender; duration of the symptoms; and, counter indications, if any, and other variables to be adjusted by the individual physician. A desired dosage can be administered in one or more applications to obtain the desired results. Pharmaceutical compositions containing the immunoproteasome inhibitors of the presently disclosed subject matter can be provided in unit dosage forms.

IV.D. Methods of Autoimmune Diseases

The presently disclosed subject matter provides methods and compositions for treating autoimmune diseases in a subject in need of treatment thereof. In some embodiments, these methods comprise administering to the subject a compound having specificity for the immunoproteasome. In some embodiments, the immunoproteasome inhibitor is a compound of Formula (I-II).

As used herein, the term "autoimmune disease" refers to a disorder wherein the immune system of a mammal mounts a humoral or cellular immune response to the mammal's own tissue or has intrinsic abnormalities in its tissues preventing proper cell survival without inflammation. Thus, autoimmune diseases can be characterized by the circulation of autoantibodies. "Autoantibodies" are antibodies that bind to proteins, cells or tissues of the individual in which the antibodies are produced. Without being bound to any particular theory, immunoproteasome inhibitors of the presently disclosed subject matter are believed to be efficacious in the treatment of autoimmune diseases through their ability to modulate NF-κB activity (i.e., modulating inflammatory responses or antigen presentation).

Examples of autoimmune diseases include, but are not limited to, diabetes, rheumatoid arthritis, multiple sclerosis, lupus erythematosis, myasthenia gravis, sclerodenna, Crohn's disease, ulcerative colitis, Hashimoto's disease, Graves' disease, Sjogren's syndrome, polyendocrine failure, vitiligo, peripheral neuropathy, graft-versus-host disease, autoimmune polyglandular syndrome type I, acute glomerulonephritis, Addison's disease, adult-onset idiopathic hypoparathyroidism (AOIH), alopecia totalis, amyotrophic lateral sclerosis, ankylosing spondylitis, autoimmune aplastic anemia, autoimmune hemolytic anemia, Behcet's disease, Celiac disease, chronic active hepatitis, CREST syndrome, dermatomyositis, dilated cardiomyopathy, eosinophilia-myalgia syndrome, epidermolisis bullosa acquisita (EBA), giant cell arteritis, Goodpasture's syndrome, Guillain-Barre syndrome, hemochromatosis, Henoch-Schonlein purpura, idiopathic IgA nephropathy, insulin-dependent diabetes mellitus (IDDM), juvenile rheumatoid arthritis, Lambert-Eaton syndrome, linear IgA dermatosis, myocarditis, narcolepsy, necrotizing vasculitis, neonatal lupus syndrome (NLE), nephrotic syndrome, pemphigoid, pemphigus, polymyositis, primary sclerosing cholangitis, psoriasis, rapidly-progressive glomerulonephritis (RPGN), Reiter's syndrome, stiff-man syndrome and thyroiditis. As used herein, the term "diabetes" refers both to the type I form of the disease and to type II cases that share only an islet cell defect with type I. Graft-versus-host disease refers to an immune response of cells taken from a donor to cells in the recipient. In particular, graft-versus-host disease can result from blood transfusions or bone marrow transplant.

Symptoms common to many types of autoimmune dysfunction include, but are not limited to: fatigue; inflammation; paresis; joint stiffness, pain or swelling; skin lesions or nodules; skin discoloration; enzymatic imbalances; and tissue degeneration. Examples of such symptoms as pertain to specific autoimmune diseases are described in U.S. Pat. No. 6,773,705, incorporated herein by reference. Such symptoms or, alternatively, measurements of tissue death/destruction, can be used either as diagnostic indicators of the presence of an autoimmune disease, or as indices by which to assess the efficacy of treatment thereof.

In the treatment of autoimmune disease, a "therapeutically effective" dose, refers to a treatment regimen sufficient to restore the subject to the basal state, as defined herein, at the cellular or tissue site of manifestation or to prevent an autoimmune disease in an individual at risk thereof or restore the subject's immune system to the basal state. As used herein, the term "basal state" refers to the level of activity of a protein, nucleic acid or other molecule where autoimmune disease is not present, i.e. a "normal level" of activity. Alternatively, a "therapeutically effective regimen" can be sufficient to arrest or otherwise ameliorate symptoms of an autoimmune disease. Generally, in the treatment of autoimmune diseases, an effective dosage regimen requires providing the medication over a period of time to achieve noticeable therapeutic effects; such a period of time can begin at, or even before, birth and continue throughout the life of the individual being treated.

IV.E. Methods of Suppressing Antigenic Peptide Presentation

In some embodiments, the presently disclosed subject matter provides a method of suppressing antigenic peptide presentation, comprising administering a compound having specificity for the immunoproteasome. Without being bound to any particular theory, the immunoproteasome is believed to be involved in the processing of internalized cellular or viral antigens into antigenic peptides that bind to MHC-I molecules on antigen presenting cells. The presently disclosed immunoproteasome inhibitors, thus, can be used to reduce or eliminate undesired responses to antigen presentation. For example, the compounds of Formula (I-II) can be used to suppress antigenic peptide presentation associated with autoimmune diseases and transplant rejection. Transplant rejection can involve cells, tissues, or an entire organ.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Materials and Methods

Reagents and starting materials for the peptide inhibitors were from Aldrich (Milwaukee, Wis., United States of America), Sigma (St. Louis, Mo., United States of America), Calbiochem (San Diego, Calif., United States of America) and Bachem Bioscience, Inc. (Philadelphia, Pa., United States of America). The synthesis of Cbz-LnL-CHO (Calpeptin; Suntory Limited, Osaka, Japan) is described in U.S. Pat. No. 5,081,284 to Higuchi. N. et al. The synthesis of Cbz-LLF-CHO is as previously described. See Vinitsky, A., et al., *Biochemistry*, 31, 9421-9428 (1992). The other peptide aldehydes were prepared analogously. For example, a commercially available Cbz-dipeptide or other amino-blocked dipeptide (e.g., a Boc-dipeptide) is elaborated using the N-hydroxysuccinimide active ester method of Anderson, G. W., et al., (*J. Am. Chem. Soc.* 86, 1839-1842 (1963)). Oxidation of the peptidyl alcohols is carried out using a modified dimethylsulfoxide-carbodiimide reaction technique. See Wilk, S. and Orlowski, M., *J. Neurochem.*, 35, 1172-1182 (1980). See also U.S. Pat. No. 5,580,654 to Orlowski, M. et al.

Example 1

In Vitro Study of Proteasome Specificity

To investigate the possibility that inhibitors specific for the immunoproteasome could be identified, the proteasome from pituitary tissue, representative of the X/Y/Z isoform (i.e., the constitutive proteasome), and the proteasome from spleen tissue, representative of the LMP-2/7/10 isoform (i.e., the immunoproteasome), were each purified to homogeneity. A panel of peptidyl-aldehyde substrate-related inhibitors were then screened for their ability to inhibit the chymotrypsin-like (ChT-L) and branched chain amino acid preferring (BrAAP) activities of these two proteasome preparations. Some peptide aldehydes, such as Cbz-LLL-CHO, also known as MG-132 (AG Scientific, Inc., San Diego, Calif., United States of America), demonstrated comparable abilities to inhibit the ChT-L and BrAAP components of both the spleen and pituitary proteasomes (see Table 1), suggesting that they were non-specific. The same was true for Cbz-FL-CHO, the peptide aldehyde version of bortezomib.

A second group of inhibitors, including Cbz-LnL-CHO, Cbz-FF-CHO, Cbz-hFF-CHO, Cbz-LF-CHO, Cbz-AF-CHO, Cbz-GPAF-CHO, and Cbz-GPFF-CHO, were able to preferentially inhibit both the ChT-L and BrAAP components of the spleen proteasome (see Table 2), while leaving the pituitary proteasome relatively unaffected. The best example of this group was Cbz-LnL-CHO, which in vitro showed a greater than 100-fold preference for the LMP-containing ChT-L proteasome activity, and a greater than 160-fold preference for the LMP-containing BrAAP proteasome activity.

Finally, two inhibitors (Cbz-LLF-CHO and Cbz-GFF-CHO) showed a mixed pattern of specificity (see Table 3), with preferential inhibition of the LMP-containing BrAAP proteasome activity, but only a modest or an indiscernible effect in inhibition of the LMP-containing ChT-L proteasome activity.

TABLE 1

Inhibition of the Spleen- and Pituitary-Derived Proteasomes with Substrate Related Peptide Aldehydes: Non-Specific Inhibitors

| Inhibitor | Component | $K_i$ (μM) Spleen Proteasome | $K_i$ (μM) Pituitary Proteasome |
|---|---|---|---|
| Non-specific inhibitors | | | |
| Cbz-LLL-CHO | ChT-L | 5.1 ± 0.9 (6) | 6.9 ± 0.84 (6) |
| | BrAAP | 6.9 ± 0.84 (6) | 6.8 ± 0.9 (12) |
| Cbz-LAL-CHO | ChT-L | 1.45 ± 1.05 (3) | 0.82 ± 0.15 (6) |
| | BrAAP | 2.14 ± 0.21 (6) | 12 ± 0.17 (3) |
| Cbz-FL-CHO | ChT-L | 2.1 ± 0.29 (9) | 5.55 ± 0.47 (6) |
| | BrAAP | 0.69 ± 0.1 (3) | 4.96 ± 0.58 (3) |

Dixon plots were used to obtain $K_i$ values. Determinations were carried out at three substrate concentrations and at six different inhibitor concentrations without preincubation of the enzyme with inhibitors. Substrate concentrations were 0.1 to 0.4 mM for the BrAAP activity of the spleen, and 0.5 to 4.0 mM for the ChT-L activity, and 1.0 to 4.0 mM for all others. The substrate for the BrAAP activity was Cbz-GPALG-pAB, and Cbz-GGF-pAB for the ChT-L activity. Data are averages±standard error, with the number of determinations shown in parentheses.

TABLE 2

Inhibition of the Spleen- and Pituitary-Derived Proteasomes with Substrate Related Peptide Aldehydes: Immunoproteasome-Specific Inhibitors

| Inhibitor | Component | $K_i$ (μM) Spleen Proteasome | $K_i$ (μM) Pituitary Proteasome |
|---|---|---|---|
| Immunoproteasome-specific inhibitors | | | |
| Cbz-LnL-CHO | ChT-L | 1.03 ± 0.17 (3) | 105 ± 1.3 (3) |
| | BrAAP | 1.45 ± 0.15 (8) | 239 ± 14 (6) |
| Cbz-FF-CHO | ChT-L | 4.0 ± 0.27 (6) | 56 ± 4.4 (3) |
| | BrAAP | 1.46 ± 0.38 (9) | NI |
| Cbz-hFF-CHO | ChT-L | 2.74 ± 0.33 (6) | 40† |
| | BrAAP | 3.19 ± 0.11 (3) | NI |
| Cbz-LF-CHO | ChT-L | 5.6 ± 0.2 (3) | 154† |
| | BrAAP | 4.07 ± 0.17 (3) | NI |
| Cbz-AF-CHO | ChT-L | 24† (2) | 380† (2) |
| | BrAAP | 24† (2) | NI† |
| Cbz-GPAF-CHO | ChT-L | 8.4 ± 0.52 (3) | 460 ± 66 (3) |
| | BrAAP | 2.6 ± 0.24 (3) | NI |
| Cbz-GPFF-CHO | ChT-L | 5.6 ± 1.1 (3) | 58 ± 1.8 (3) |
| | BrAAP | 1.2 ± 0.07 (3) | 310 ± 44 (3) |

Dixon plots were used to obtain $K_i$ values. Determinations were carried out at three substrate concentrations and at six different inhibitor concentrations without preincubation of the enzyme with inhibitors. Substrate concentrations were 0.1 to 0.4 mM for the BrMP activity of the spleen, and 0.5 to 4.0 mM for the ChT-L activity, and 1.0 to 4.0 mM for all others. The substrate for the BrAAP activity was Cbz-GPALG-pAB, and Cbz-GGF-pAB for the ChT-L activity. Data are averages±standard error, with the number of determinations shown in parentheses. † indicates $IC_{50}$ instead of $K_i$. NI indicates no inhibition in the tested range.

TABLE 3

Inhibition of the Spleen- and Pituitary-Derived Proteasomes with Substrate Related Peptide Aldehydes: Mixed Immunoproteasome-Specific Inhibitors

| Inhibitor | Component | $K_i$ (μM) Spleen Proteasome | $K_i$ (μM) Pituitary Proteasome |
|---|---|---|---|
| Mixed immunoproteasome-specific inhibitors | | | |
| Cbz-LLF-CHO | ChT-L | 5.97 ± 1.4 (12) | 1.6 ± 0.5 (3) |
| | BrAAP | 0.79 ± 0.09 (6) | 110 ± 9.2 (4) |
| Cbz-GFF-CHO | ChT-L | 1.03† | 2.7† |
| | BrAAP | 5.3† | 369† |

Dixon plots were used to obtain $K_i$ values. Determinations were carried out at three substrate concentrations and at six different inhibitor concentrations without preincubation of the enzyme with inhibitors. Substrate concentrations were 0.1 to 0.4 mM for the BrAAP activity of the spleen, and 0.5 to 4.0 mM for the ChT-L activity, and 1.0 to 4.0 mM for all others. The substrate for the BrAAP activity was Cbz-GPALG-pAB, and Cbz-GGF-pAB for the ChT-L activity. Data are averages±standard error, with the number of determinations shown in parentheses. † indicates $IC_{50}$ instead of $K_i$. NI indicates no inhibition in the tested range.

Example 2

Immunoproteasome Expression in Cancer Cell Lines

Protein extracts were prepared from NCI-H929 human myeloma cells, IM-9 human B-lymphoblasts, HPAC human pancreatic adenocarcinoma cells, and Hs 294T human melanoma cells. The protein extracts were then subjected to Western blotting for the detection of the LMP-2 subunit, and then stripped and reprobed with antibodies recognizing HSC-70.

As illustrated in FIG. 1, LMP-2 is expressed in both of the B-lymphocyte lineage-derived cells, but virtually absent in the pancreatic carcinoma and melanoma cell lines. This observation supports that expression of the proteasome containing LMP-2/7/10 subunits is relatively restricted to cells of lymphatic origin in comparison with other cell lines. In addition, it indicates that the process of transformation in at least these two solid tumors has not activated expression of LMP-2 subunits. HSC-70 serves as a control to verify equal protein loading in all of the lanes.

Example 3

Proteasome Inhibitor-Induced Apoptosis

Figure 2:
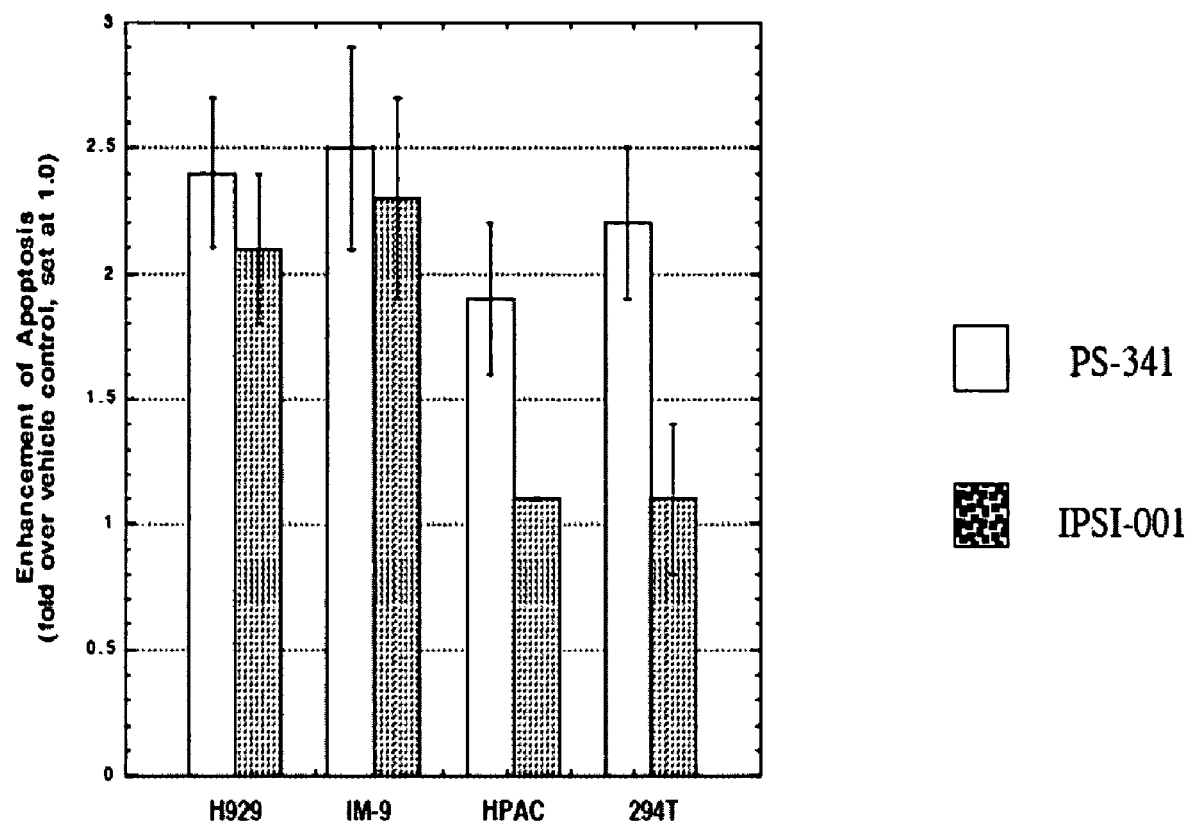
FIG. 2 is a bar graph illustrating the induction of apoptosis by bortezomib (PS-341; open bars) and Cbz-LnL-CHO (immunoproteasome specific inhibitor (IPSI)-001; stippled bars) in the cancer cell lines described in the description of FIG. 1.

Cultured NCI-H929 human myeloma cells, IM-9 human B-lymphoblasts, HPAC human pancreatic adenocarcinoma cells, and Hs 294T human melanoma cells were exposed to vehicle, 5 nM bortezomib (PS-341), or 50 μM Cbz-LnL-CHO for 18 hours. Apoptosis was evaluated using an enzyme-linked immunosorbent assay that detects apoptotic nuclear DNA fragmentation. Cell death is expressed as the fold-increase in apoptosis over the vehicle control, which was arbitrarily set at 1.0. Referring now to FIG. 2, the effect of PS-341 is shown in the open bar graphs, while Cbz-LnL-CHO (IPSI-001) is in the stippled bar graphs. The mean and standard error of the mean are shown for each condition from four independent experiments.

Bortezomib, a non-specific proteasome inhibitor, induces apoptosis roughly equally in all of the cell lines tested. Cbz-LnL-CHO, which is able to preferentially inhibit only proteasomes containing the LMP-2/7/10 subunits, induces significant apoptosis only in H929 and IM-9 cell lines, and not in the melanoma and pancreatic carcinoma cells. Note that this pattern of apoptosis parallels the expression pattern for LMP-2 shown in the Western blot in FIG. 1. This observation indicates that Cbz-LnL-CHO is an agent that can preferentially inhibit and induce apoptosis in immunoproteasome-containing cell lines.

Example 4

Immunoproteasome Tissue Expression

Protein extracts were prepared from commercially available brain, lung, renal, and spleen tissue using standard techniques, and then subjected to Western blotting for the detection of the LMP-2 subunit. The protein extracts were then stripped and reprobed with antibodies recognizing the Z subunit of the proteasome, and finally with antibodies recognizing actin. See FIG. 3.

Figure 3:
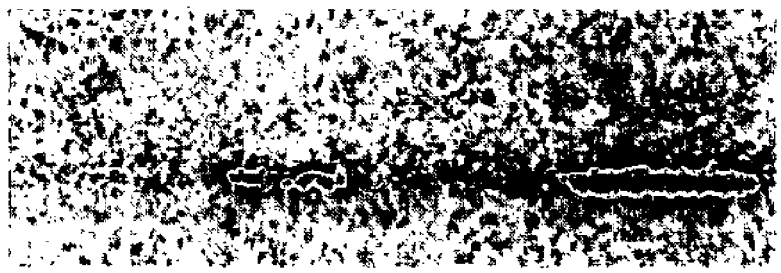
FIG. 3 is a Western blot showing the expression of the LMP-2 and Z proteasome subunits in brain, lung, kidney, and spleen tissue.
Figure 3:
Figure 3:

As shown in FIG. 3, a high level of expression of LMP-2 is seen in spleen tissue, and possibly a low level of expression in lung tissue, but LMP-2 is virtually absent in the brain and kidney. In contrast, the Z-subunit is absent in spleen tissue, but expressed at high levels in the other three tissues. This observation indicates that expression of the proteasome containing LMP-2/7/10 subunits is relatively restricted to the spleen in this sampling of tissues. Actin serves as a control to verify equal protein loading in all of the lanes.

For immunoproteasome inhibitors to be effective anti-tumor agents they should show an ability to preferentially induce cell death in lines expressing LMP-2/7/10 proteasomes, while relatively sparing cell lines expressing X/Y/Z proteasomes. To this end, the LMP-containing NCI-H929 multiple myeloma cell line, see Hollis, G. F. et al., *Mol. Cell. Biol.,* 8: 124-129 (1988), and the IM-9 lymphoblastoid cell line, see Fahey, J. L. et al., *Ann. N.Y. Acad. Sci.,* 190: 221-234 (1971), as well as the X/Y/Z-containing HPAC pancreatic carcinoma cell line, see Norman, J., et al., *J. Surg. Res.,* 57: 33-38 (1994), and the Hs 294T melanoma cell line, see Creasey, A. A., et al., *In Vitro,* 15: 342-350 (1979), were tested (see FIG. 1 for studies of subunit expression). While non-specific inhibitors such as PS-341 induced apoptosis to a roughly equivalent extent in all four cell lines (see FIG. 2), the immunoproteasome-specific agent Cbz-LnL-CHO activated programmed cell death only in the myeloma and lymphoblastoid cell line, while leaving the other two unaffected. These results indicate that Cbz-LnL-CHO based drugs have the ability to induce apoptosis and exhibit anti-tumor efficacy specifically in tumors expressing the LMP-2/7/10-type proteasome. These agents should relatively spare neural tissues, which do not express LMP proteasomes (see FIG. 3), likely averting the development of neurotoxicity in patients.

REFERENCES

The references listed below as well as all references cited in the specification are incorporated herein by reference to the extent that they supplement, explain, provide a background for or teach methodology, techniques and/or compositions employed herein.

Voorhees, P. M., Dees, E. C., O'Neil, B., and Orlowski, R. Z., The proteasome as a target for cancer therapy. *Clin. Cancer Res.,* 9: 6316-6325 (2003).

Adams, J., Palombella, V. J., Sausville, E. A., Johnson, J., Destree, A., Lazarus, D. D., Maas, J., Pien, C. S., Prakash, S., and Elliott, P. J., Proteasome inhibitors: A novel class of potent and effective anti-tumor agents. *Cancer Res.,* 59: 2615-2622 (1999). Orlowski, R. Z., Stinchcombe, T. E., Mitchell, B. S., Shea, T. C., Baldwin, A. S., Stahl, S., Adams, J., Esseltine, D. L., Elliott, P. J., Pien, C. S., Guerciolini, R., Anderson, J. K., Depcik-Smith, N. D., Bhagat, R., Lehman, M. J., Novick, S. C., O'Connor, O. A., and Soignet, S. L., Phase I trial of the proteasome inhibitor PS-341 in patients with refractory hematologic malignancies. *J. Clin. Oncol.*, 20: 4420-4427 (2002).

Richardson, P. G., Barlogie, B., Berenson, J., Singhal, S., Jagannath, S., Irwin, D., Rajkumar, S. V., Srkalovic, G., Alsina, M., Alexanian, R., Siegel, D., Orlowski, R. Z., Kuter, D., Limentani, S. A., Lee, S., Hideshima, T., Esseltine, D. L., Kauffman, M., Adams, J., Schenkein, D. P., and Anderson, K. C., A phase 2 study of bortezomib in relapsed, refractory myeloma. *N. Engl. J. Med.*, 348:2609-2617 (2003).

Fruh, K., Gossen, M., Wang, K., Bujard, H., Peterson, P. A., and Yang, Y., Displacement of housekeeping proteasome subunits by MHC-encoded LMPs: A newly discovered mechanism for modulating the multi-catalytic proteinase complex. *EMBO J.*, 13: 3236-3244 (1994).

Akiyama, K., Yokota, K., Kagawa, S., Shimbara, N., Tamura, T., Akioka, H., Nothwang, H. G., Noda, C., Tanaka, K., and Ichihara, A., cDNA cloning and interferon gamma down-regulation of proteasomal subunits X and Y. *Science*, 265: 1231-1234 (1994).

Akiyama, K., Kagawa, S., Tamura, T., Shimbara, N., Takashina, M., Kristensen, P., Hendil, K. B., Tanaka, K., and Ichihara, A., Replacement of proteasome subunits X and Y by LMP7 and LMP2 induced by interferon-gamma for acquirement of the functional diversity responsible for antigen processing. *FEBS Lett.*, 343: 85-88 (1994).

Belich, M. P., Glynne, R. J., Senger, G., Sheer, D., and Trowsdale, J., Proteasome components with reciprocal expression to that of the MHC-encoded LMP proteins. *Curr. Biol.*, 4: 7697-776 (1994).

Tanaka, K., Role of proteasomes modified by interferon-gamma in antigen processing. *J. Leukoc. Biol.*, 56: 571-575 (1994).

Teoh, C. Y. and Davies, K. J., Potential roles of protein oxidation and the immunoproteasome in MHC class I antigen presentation: The 'PrOxI' hypothesis. *Arch. Biochem. Biophys.*, 423: 88-96 (2004).

Wong, C., Morse, M., and Nair, S. K., Induction of primary, human antigen-specific cytotoxic T lymphocytes in vitro using dendritic cells pulsed with peptides. *J. Immunother.*, 21: 32-40 (1998).

El-Shami, K. M., Tirosh, B., Popovic, D., Carmon, L., Tzehoval, E., Vadai, E., Feldman, M., and Eisenbach, L., Induction of anti-tumor immunity by proteasome-inhibited syngeneic fibroblasts pulsed with a modified TAA peptide. *Int. J. Cancer*, 85: 236-242 (2000).

Hollis, G. F., Gazdar, A. F., Bertness, V., and Kirsch, I. R., Complex translocation disrupts c-myc regulation in a human plasma cell myeloma. *Mol. Cell. Biol.*, 8: 124-129 (1988).

Fahey, J. L., Buell, D. N., and Sox, H. C., Proliferation and differentiation of lymphoid cells: Studies with human lymphoid cell lines and immunoglobulin synthesis. *Ann. N.Y. Acad. Sci.*, 190:221-234 (1971).

Norman, J., Franz, M., Schiro, R., Nicosia, S., Docs, J., Fabri, P. J., and Gower, W. R., Jr., Functional glucocorticoid receptor modulates pancreatic carcinoma growth through an autocrine loop. *J. Surg. Res.*, 57: 33-38 (1994).

Creasey, A. A., Smith, H. S., Hackett, A. J., Fukuyama, K., Epstein, W. L., and Madin, S. H., Biological properties of human melanoma cells in culture. *In Vitro*, 15: 342-350 (1979).

Kisselev, A. F. and Goldberg, A. L., Proteasome inhibitors: From research tools to drug candidates. *Chem. Biol.*, 8: 739-758 (2001).

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A compound having a 10-fold or greater preference for inhibiting an immunoproteasome as compared to a constitutive proteasome, wherein the compound is selected from the group consisting of:
    N-carbobenzyloxy-phenylalanyl-phenylalanylal,
    N-carbobenzyloxy-homophenylalanyl-phenylalanylal,
    N-carbobenzyloxy-alanyl-phenylalanylal,
    N-carbobenzyloxy-glycyl-prolyl-alanyl-phenylalanylal,
    N-carbobenzyloxy-glycyl-prolyl-phenylalanyl-phenylalanylal,
    N-carbobenzyloxy-glycyl-phenylalanyl-phenylalanylal,
    N-carbobenzyloxy-leucyl-norleucine boronic acid,
    N-carbobenzyloxy-phenylalanyl-phenylalanine boronic acid,
    N-carbobenzyloxy-homophenylalanyl-phenylalanine boronic acid,
    N-carbobenzyloxy-leucyl-phenylalanine boronic acid,
    N-carbobenzyloxy-glycyl-prolyl-alanyl-phenylalanine boronic acid,
    N-carbobenzyloxy-glycyl-prolyl-phenylalanyl-phenylalanine boronic acid,
    N-carbobenzyloxy-leucyl-leucyl-phenylalanine boronic acid,
    N-carbobenzyloxy-glycyl-phenylalanyl-phenylalanine boronic acid,
    N-carbobenzyloxy-leucyl-norleucine methyl vinyl sulfone,
    N-carbobenzyloxy-phenylalanyl-phenylalanine methyl vinyl sulfone,
    N-carbobenzyloxy-homophenylalanyl-phenylalanine methyl vinyl sulfone,
    N-carbobenzyloxy-leucyl-phenylalanine methyl vinyl sulfone,
    N-carbobenzyloxy-alanyl-phenylalanine methyl vinyl sulfone,
    N-carbobenzyloxy-glycyl-prolyl-alanyl-phenylalanine methyl vinyl sulfone,
    N-carbobenzyloxy-glycyl-prolyl-phenylalanyl-phenylalanine methyl vinyl sulfone,
    N-carbobenzyloxy-leucyl-leucyl-phenylalanine methyl vinyl sulfone,
    N-carbobenzyloxy-glycyl-phenylalanyl-phenylalanine methyl vinyl sulfone,
    N-carbobenzyloxy-leucyl-norleucine epoxy ketone,
    N-carbobenzyloxy-phenylalanyl-phenylalanine epoxy ketone,
    N-carbobenzyloxy-homophenylalanyl-phenylalanine epoxy ketone,
    N-carbobenzyloxy-leucyl-phenylalanine epoxy ketone,
    N-carbobenzyloxy-alanyl-phenylalanine epoxy ketone,
    N-carbobenzyloxy-glycyl-prolyl-alanyl-phenylalanine epoxy ketone,
    N-carbobenzyloxy-glycyl-prolyl-phenylalanyl-phenylalanine epoxy ketone,
    N-carbobenzyloxy-leucyl-leucyl-phenylalanine epoxy ketone, and
    N-carbobenzyloxy-glycyl-phenylalanyl-phenylalanine epoxy ketone; or
a pharmaceutically acceptable salt thereof.

* * * * *

UNITED STATES PATENT AND TRADEMARK OFFICE
CERTIFICATE OF CORRECTION

PATENT NO. : 7,589,066 B2
APPLICATION NO. : 11/374652
DATED : September 15, 2009
INVENTOR(S) : Orlowski et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 141 days.

Signed and Sealed this

Twenty-first Day of September, 2010

David J. Kappos
*Director of the United States Patent and Trademark Office*